United States Patent
Ewen et al.

(10) Patent No.: US 6,635,779 B1
(45) Date of Patent: *Oct. 21, 2003

(54) METALLOCENE COMPOUNDS, PROCESS FOR THEIR PREPARATION AND THEIR USE IN CATALYTIC SYSTEMS FOR THE POLYMERIZATION OF OLEFINS

(75) Inventors: John A. Ewen, Houston, TX (US); Michael J. Elder, Heidelberg-Kirchheim (DE); Robert L. Jones, Kirchheim (DE)

(73) Assignee: Basell Technology Company bv, Hoofddorp (NL)

(*) Notice: Subject to any disclaimer, the term of this patent is extended or adjusted under 35 U.S.C. 154(b) by 56 days.

This patent is subject to a terminal disclaimer.

(21) Appl. No.: 09/913,742

(22) PCT Filed: Dec. 7, 2000

(86) PCT No.: PCT/EP00/12406
§ 371 (c)(1),
(2), (4) Date: Nov. 20, 2001

(87) PCT Pub. No.: WO01/44318
PCT Pub. Date: Jun. 21, 2001

Related U.S. Application Data

(63) Continuation-in-part of application No. 09/461,858, filed on Dec. 15, 1999.

(51) Int. Cl.[7] .............................. C07F 17/00; C07F 7/00; B01J 31/00; C08F 4/44
(52) U.S. Cl. .............................. 556/11; 556/12; 556/21; 556/28; 556/30; 556/43; 556/53; 556/56; 556/70; 556/87; 556/406; 534/11; 534/15; 549/3; 549/32; 502/103; 502/117; 526/160; 526/943; 526/128; 526/149; 526/150; 526/348.1; 526/348.5; 526/351; 526/352
(58) Field of Search .............................. 556/11, 12, 21, 556/28, 30, 43, 53, 58, 70, 87, 406; 534/11, 15; 349/3, 32; 502/103, 117; 526/128, 149, 150, 160, 348.1, 348.5, 351, 352, 943

(56) References Cited

U.S. PATENT DOCUMENTS 6,444,833 B1 * 9/2002 Ewen et al. .................. 556/11

FOREIGN PATENT DOCUMENTS

| WO | WO 98/22486 | * | 5/1998 |
| WO | WO 99/24446 | * | 5/1999 |

OTHER PUBLICATIONS

Ewen et al., Journal Of American Chemicla Society, vol. 120, No. 41, pp. 10786–10787 (1998).*

Ewen et al., J. Am. Chem. Soc., vol. 120, No. 41, pp. 10786–10787 (published on the Web Oct. 7, 1998).*

* cited by examiner

Primary Examiner—Porfirio Nazario-Gonzalez
(74) Attorney, Agent, or Firm—Bryan Cave LLP

(57) ABSTRACT

A class of metallocene compounds is disclosed having general formula (I) wherein Y is a moiety of formula (II) wherein A, B, and D, same or different from each other, are selected from an element of the groups 14 to 16 of the Periodic Table of the Elements (new IUPAC version), with the exclusion of nitrogen and oxygen; $R^1$, $R^2$, $R^3$, $R^4$ and $R^5$ are hydrogen or hydrocarbon groups, Z is selected from a moiety of formula (II) as described above and from a moiety of formula (III) wherein $R^6$, $R^7$, $R^8$ and $R^9$, are hydrogen or hydrocarbon groups; L is a divalent bridging group; M is an atom of a transition metal selected from those belonging to group 3, 4, 5, 6 or to the lanthanide or actinide groups in the Periodic Table of the Elements (new IUPAC version), X, same or different, is hydrogen, a halogen, a $R^{10}$, $OR^{10}$, $OSO_2CF_3$, $OCOR^{10}$, $SR^{10}$, $NR^{10}_2$ or $PR^{10}_2$ group, wherein the substituents $R^{10}$ are hydrogen or alkyl groups; p is an integer of from 1 to 3, being equal to the oxidation state of the metal M minus 2. The above metallocenes are particularly useful in the polymerization of propylene.

38 Claims, No Drawings

METALLOCENE COMPOUNDS, PROCESS FOR THEIR PREPARATION AND THEIR USE IN CATALYTIC SYSTEMS FOR THE POLYMERIZATION OF OLEFINS

This application is a continuation-in-part of Ser. No. 09/461,858 filed Dec. 15, 1999.

FIELD OF THE INVENTION

The present invention relates to a new class of metallocene compounds, to a catalyst for the polymerization of olefins containing them and to a polymerization process carried out in the presence of said catalyst. The invention also relates to the corresponding ligands useful as intermediates in the synthesis of said metallocene compounds, as well as to processes for preparing said ligands and said metallocene compounds.

DESCRIPTION OF THE PRIOR ART

Metallocene compounds with two cyclopentadienyl groups are known as catalyst components for the polymerization of olefins. European Patent 129,368, for instance, describes a catalyst system for the polymerization of olefins comprising (a) a biscyclopentadienyl coordination complex with a transition metal and (b) an alumoxane. The two cyclopentadienyl groups can be linked by a divalent group.

More recently, heterocyclic metallocene compounds used in the polymerization of alpha-olefins have been described. For example, U.S. Pat. No. 5,489,659 relates to a class of silicon-containing metallocene compounds for the polymerization of alpha-olefins wherein the silicon atom is part of a non-aromatic ring condensed to the cyclopentadienyl ring. Metallocenes of this type are used in the polymerization of propylene. The activity of these metallocene-based catalysts is not satisfactory.

In International application WO 98/22486 it is described a class of metallocenes containing a cyclopentadienyl radical directly coordinating the central metal atom, to which are fused one or more rings containing at least one heteroatom. These metallocenes, in combination with a suitable cocatalyst, are used in the polymerization of olefins, such as propylene. However, the molecular weights that can be obtained at polymerization temperatures of industrial interest are still too low for most utilization and the activity of those catalyst systems, when used in the polymerization of propylene, is not satisfactory.

It would be desirable to provide a novel class of metallocenes which, when used in catalysts for the polymerization of olefins, in particular of propylene, have high activity such that the amount of the catalyst remaining in the formed polymer is minimized. Furthermore high-activity catalyst capable of yielding polymers endowed with high molecular weight, narrow molecular weight distribution as well as a high degree of isotacticity and thus of crystallinity would be desirable.

A novel class of metallocene compounds has now been unexpectedly found, which achieves the above and other results.

According to a first aspect, the present invention provides a metallocene compound of the general formula (I):

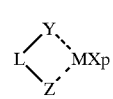
(I)

wherein
Y is a moiety of formula (II)

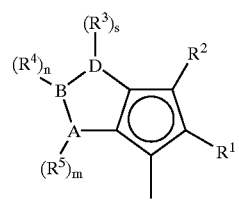
(II)

wherein
A, B and D, same or different from each other, are selected from an element of the groups 14 to 16 of the Periodic Table of the Elements (new IUPAC version), with the exclusion of nitrogen and oxygen;
$R^1$, $R^2$, $R^3$, $R^4$ and $R^5$, same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13–17 of the Periodic Table of the Elements; wherein two $R^3$ can form a ring comprising 4 to 8 atoms, or $R^3$ and $R^4$ can form a ring comprising 4 to 8 atoms, which can bear substituents; with the proviso that when s is 0 or when $R^3$ is hydrogen, $R^2$ is not hydrogen;
m, n and s, equal to or different from each other, are selected from 0, 1 and 2;
m, n and s being 0 when respectively A, B and D are selected from an element of the group 16 of the Periodic Table of the Elements (new IUPAC version);
m, n and s being 1 when respectively A, B and D are selected from an element of the group 15 of the Periodic Table of the Elements (new IUPAC version);
m, n and s being 1 or 2 when respectively A, B and D are selected from an element of the group 14 of the Periodic Table of the Elements (new IUPAC version);
and wherein the ring containing A, B and D can have double bonds in any of the allowed positions, having an aromatic character;
Z is selected from a moiety of formula (II) as described above and from a moiety of formula (III):

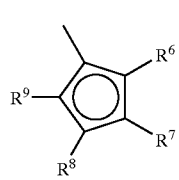
(III)

wherein $R^6$, $R^7$, $R^8$ and $R^9$, same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13–17 of the Periodic Table of the Elements, $R^7$ being different from hydrogen; optionally $R^6$ and $R^7$ or $R^7$ and $R^8$ can form a ring comprising 4 to 8 carbon atoms, which can bear substituents;

and when Z is a moiety of formula (II), Y and Z can be the same or different from each other;

L is a divalent bridging group; preferably selected from the group consisting of $C_1$–$C_{20}$ alkylidene, $C_3$–$C_{20}$ cycloalkylidene, $C_6$–$C_{20}$ arylidene, $C_7$–$C_{20}$ alkylarylidene, $C_7$–$C_{20}$ arylalkylidene optionally containing heteroatoms belonging to groups 13–17 of the Periodic Table of the Elements and silylidene containing up to 5 silicon atoms such as $SiMe_2$, $SiP_2$, $SiMe_2SiMe_2$ radical;

M is an atom of a transition metal selected from those belonging to group 3, 4, 5, 6 or to the lanthanide or actinide groups in the Periodic Table of the Elements (new IUPAC version), X, same or different, is a hydrogen atom, a halogen atom, a $R^{10}$, $OR^{10}$, $OSO_2CF_3$, $OCOR^{10}$, $SR^{10}$, $NR^{10}_2$ or $PR^{10}_2$ group, wherein the substituents $R^{10}$ are selected from the group consisting of $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radical, optionally containing heteroatoms belonging to groups 13–17 of the Periodic Table of the Elements;

p is an integer of from 0 to 3, preferably from 1 to 3, being equal to the oxidation state of the metal M minus 2, preferably p is 2;

The transition metal M is preferably titanium, zirconium or hafnium. More preferably it is zirconium;

Preferably the substituents X are chlorine atoms, methyl groups or benzyl groups.

Preferably the divalent bridging group L is $>Si(R^{17})_2$ or $>C(R^{17})_2$, wherein $R^{17}$, equal or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13–17 of the Periodic Table of the Elements; and wherein two $R^{17}$ can form a cycle comprising from 3 to 8 atoms, that can bear substituents.

More preferably the divalent bridging group L is selected from the group consisting of $>Si(CH_3)_2$, $>Si(C_6H_5)_2$, $>CH_2$ and $>C(CH_3)_2$.

Preferably A is selected from sulfur, selenium, tellurium and polonium, more preferably it is sulfur.

Preferably B and D are selected from the group 14 of the Periodic Table of the Elements (new IUPAC version), more preferably they are carbon atoms.

When Z is a moiety of formula (III) it is preferably selected among those of formula (IV):

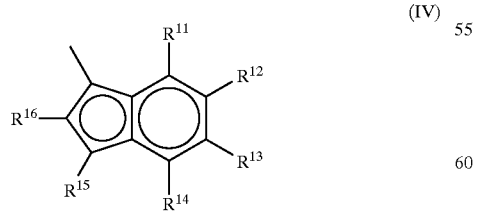

(IV)

wherein $R^{11}$, $R^{12}$, $R^{13}$, $R^{14}$, $R^{15}$ and $R^{16}$, same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13–17 of the Periodic Table of the Elements, optionally $R^{11}$ and $R^{12}$, or $R^{12}$ and $R^{13}$, or $R^{13}$ and $R^{14}$ can form a ring comprising 4 to 8 atoms which can bear substituents. Preferably $R^{14}$ and $R^{16}$ are different from hydrogen. More preferably $R^{14}$ is a $C_6$–$C_{20}$-aryl group, such as a phenyl or naphtyl group, and $R^{16}$ is a $C_1$–$C_{20}$-alkyl group, such as a methyl group.

Non limiting examples of the metallocenes of the present invention are:

dimethylsilandiylbis-6-(3-methylcyclopentadienyl-[1,2-b]-thiophene)zirconium dichloride and methyl;

dimethylsilandiylbis-6-(4-methylcyclopentadienyl-[1,2-b]-thiophene)zirconium dichloride and methyl;

dimethylsilandiylbis-6-(4-isopropylcyclopentadienyl-[1,2-b]-thiophene)zirconium dichloride and methyl;

dimethylsilandiylbis-6-(4-ter-butylcyclopentadienyl-[1,2-b]-thiophene)zirconium dichloride and methyl;

dimethylsilandiylbis-6-(3-isopropylcyclopentadienyl-[1,2-b]-thiophene)zirconium dichloride and methyl;

dimethylsilandiylbis-6-(3-phenylcyclopentadienyl-[1,2-b]-thiophene)zirconium dichloride and methyl;

dimethylsilandiylbis-6-(2,5-dimethyl-3-phenyl-cyclopentadienyl-[1,2-b]-thiophene)zirconium dichloride and methyl;

dimethylsilandiylbis-6-[2,5-dimethyl-3-(2-methylphenyl)cyclopentadienyl-[1,2-b]-thiophene]zirconium dichloride and methyl;

dimethylsilandiylbis-6-[2,5-dimethyl-3-(2,4,6-trimethylphenyl)cyclopentadienyl-[1,2-b]-thiophene]zirconium dichloride and methyl;

dimethylsilandiylbis-6-[2,5-dimethyl-3-mesitylene-cyclopentadienyl-[1,2-b]-thiophene]zirconium dichloride and methyl;

dimethylsilandiylbis-6-(2,4,5-dimethyl-3-phenylcyclopentadienyl-[1,2-b]-thiophene)zirconium dichloride and methyl;

dimethylsilandiylbis6-(2,5-diethyl-3-phenylcyclopentadienyl-[1,2-b]-thiophene)zirconium dichloride and methyl;

dimethylsilandiylbis-6-(2,5-diisopropyl-3-phenylcyclopentadienyl-[1,2-b]-thiophene)zirconium dichloride and methyl;

dimethylsilandiylbis-6-(2,5-diter-butyl-3-phenylcyclopentadienyl-[1,2-b]-thiophene)zirconium dichloride and methyl;

dimethylsilandiylbis-6-(2,5-ditrimethylsilyl-3-phenylcyclopentadienyl-[1,2-b]-thiophene)zirconium dichloride and methyl;

dimethylsilandiylbis-6-(3-methylcyclopentadienyl-[1,2-b]-silole)zirconium dichloride and methyl;

dimethylsilandiylbis-6-(3-isopropylcyclopentadienyl-[1,2-b]-silole)zirconium dichloride and methyl;

dimethylsilandiylbis-6-(3-phenylcyclopentadienyl-[1,2-b]-silole)zirconium dichloride and methyl;

dimethylsilandiylbis-6-(2,5-dimethyl-3-phenyl-cyclopentadienyl-[1,2-b]-silole)zirconium dichloride and methyl;

dimethylsilandiylbis-6-[2,5-dimethyl-3-(2-methylphenyl)cyclopentadienyl-[1,2-b]-silole]zirconium dichloride and methyl;

dimethylsilandiylbis-6-[2,5-dimethyl-3-(2,4,6-trimethylphenyl)cyclopentadienyl-[1,2-b]-silole]zirconium dichloride and methyl;

dimethylsilandiylbis-6-[2,5-dimethyl-3-mesitylenecyclopentadienyl-[1,2-b]-silole]zirconium dichloride and methyl;

dimethylsilandiylbis-6-(2,4,5-trimethyl-3-phenylcyclopentadienyl-[1,2-b]-silole)zirconium dichloride and methyl;

dimethylsilandiylbis-6-(2,5-diethyl-3-phenylcyclopentadienyl-[1,2-b]-silole)zirconium dichloride and methyl;

dimethylsilandiylbis-6-(2,5-diisopropyl-3-phenylcyclopentadienyl-[1,2-b]-silole)zirconium dichloride and methyl;

dimethylsilandiylbis-6-(2,5-diter-butyl-3-phenylcyclopentadienyl-[1,2-b]-silole)zirconium dichloride and methyl;

dimethylsilandiylbis-6-(2,5-ditrimethylsilyl-3-phenylcyclopentadienyl-[1,2-b]-silole)zirconium dichloride and methyl;

dimethylsilandiylbis-6-(3-methylcyclopentadienyl-[1,2-b]-tellurophene)zirconium dichloride and methyl;

dimethylsilandiylbis-6-(3-isopropylcyclopentadienyl-[1,2-b]-tellurophene)zirconium dichloride and methyl;

dimethylsilandiylbis-6-(3-phenylcyclopentadienyl-[1,2-b]-tellurophene)zirconium dichloride and methyl;

dimethylsilandiylbis-6-(2,5-dimethyl-3-phenylcyclopentadienyl-[1,2-b]-tellurophene)zirconium dichloride and methyl;

dimethylsilandiylbis-6-[2,5-dimethyl-3-(2-methylphenyl)cyclopentadienyl-[1,2-b]-tellurophene]zirconium dichloride and methyl;

dimethylsilandiylbis-6-[2,5-dimethyl-3-(2,4,6-trimethylphenyl)cyclopentadienyl-[1,2-b]-tellurophene]zirconium dichloride and methyl;

dimethylsilandiylbis-6-[2,5-dimethyl-3-mesitylenecyclopentadienyl-[1,2-b]-tellurophene]zirconium dichloride and methyl;

dimethylsilandiylbis-6-(2,4,5-trimethyl-3-phenylcyclopentadienyl-[1,2-b]-tellurophene)zirconium dichloride and methyl;

dimethylsilandiylbis-6-(2,5-diethyl-3-phenylcyclopentadienyl-[1,2-b]-tellurophene)zirconium dichloride and methyl;

dimethylsilandiylbis-6-(2,5-diisopropyl-3-phenylcyclopentadienyl-[1,2-b]-tellurophene)zirconium dichloride and methyl;

dimethylsilandiylbis-6-(2,5-diter-butyl-3-phenylcyclopentadienyl-[1,2-b]-tellurophene)zirconium dichloride and methyl;

dimethylsilandiylbis-6-(2,5-ditrimethylsilyl-3-phenylcyclopentadienyl-[1,2-b]-tellurophene)zirconium dichloride and methyl;

dimethylsilandiylbis-6-(3-methylcyclopentadienyl-[1,2-b]-tellurophene)zirconium dichloride and methyl;

dimethylsilandiylbis-6-(3-isopropylcyclopentadienyl-[1,2-b]-tellurophene)zirconium dichloride and methyl;

dimethylsilandiylbis-6-(3-phenylcyclopentadienyl-[1,2-b]-tellurophene)zirconium dichloride and methyl;

dimethylsilandiylbis-6-(2,5-dimethyl-3-phenylcyclopentadienyl-[1,2-b]-tellurophene)zirconium dichloride and methyl;

dimethylsilandiylbis-6-[2,5-dimethyl-3-(2-methylphenyl)cyclopentadienyl-[1,2-b]-tellurophene]zirconium dichloride and methyl;

dimethylsilandiylbis-6-[2,5-dimethyl-3-(2,4,6-trimethylphenyl)cyclopentadienyl-[1,2-b]-tellurophene]zirconium dichloride and methyl;

dimethylsilandiylbis-6-[2,5-dimethyl-3-mesitylenecyclopentadienyl-[1,2-b]-tellurophene]zirconium dichloride and methyl;

dimethylsilandiylbis-6-(2,4,5-trimethyl-3-phenylcyclopentadienyl-[1,2-b]-tellurophene)zirconium dichloride and methyl;

dimethylsilandiylbis-6-(2,5-diethyl-3-phenylcyclopentadienyl-[1,2-b]-tellurophene)zirconium dichloride and methyl;

dimethylsilandiylbis-6-(2,5-diisopropyl-3-phenylcyclopentadienyl-[1,2-b]-tellurophene)zirconium dichloride and methyl;

dimethylsilandiylbis-6-(2,5-diter-3-butyl-3-phenylcyclopentadienyl-[1,2-b]-tellurophene)zirconium dichloride and methyl;

dimethylsilyl-6-(2,5-dimethyl-3-phenylcyclopentadienyl-[1,2-b]-tellurophene)-1-(2-methyl-4-phenylindenyl)zirconium dichloride and methyl;

dimethylsilandiylbis-6-(2,5-ditrimethylsilyl-3-phenylcyclopentadienyl-[1,2-b]-tellurophene)zirconium dichloride and methyl;

dimethylsilandiylbis-6-(3-methylcyclopentadienyl-[1,2-b]-phosphole)zirconium dichloride and methyl;

dimethylsilandiylbis-6-(3-isopropylcyclopentadienyl-[1,2-b]-phosphole)zirconium dichloride and methyl;

dimethylsilandiylbis-6-(3-phenylcyclopentadienyl-[1,2-b]-phosphole)zirconium dichloride and methyl;

dimethylsilandiylbis-6-(2,5-dimethyl-3-phenylcyclopentadienyl-[1,2-b]-phosphole)zirconium dichloride and methyl;

dimethylsilandiylbis-6-[2,5-dimethyl-3-(2-methylphenyl)cyclopentadienyl-[1,2-b]-phosphole]zirconium dichloride and methyl;

dimethylsilandiylbis-6-[2,5-dimethyl-3-(2,4,6-trimethylphenyl)cyclopentadienyl-[1,2-b]-phosphole]zirconium dichloride and methyl;

dimethylsilandiylbis-6-[2,5-dimethyl-3-mesitylenecyclopentadienyl-[1,2-b]-phosphole]zirconium dichloride and methyl;

dimethylsilandiylbis-6-(2,4,5-trimethyl-3-phenylcyclopentadienyl-[1,2-b]-phosphole)zirconium dichloride and methyl;

dimethylsilandiylbis-6-(2,5-diethyl-3-phenylcyclopentadienyl-[1,2-b]-phosphole)zirconium dichloride and methyl;

dimethylsilandiylbis-6-(2,5-diisopropyl-3-phenylcyclopentadienyl-[1,2-b]-phosphole)zirconium dichloride and methyl;

dimethylsilandiylbis-6-(2,5-diter-butyl-3-phenylcyclopentadienyl-[1,2-b]-phosphole)zirconium dichloride and methyl;

dimethylsilyl-6-(2,5-dimethyl-3-phenylcyclopentadienyl-[1,2-b]-phosphole)-1-(2-methyl-4-phenylindenyl)zirconium dichloride and methyl;

dimethylsilandiylbis-6-(2,5-ditrimethylsilyl-3-phenylcyclopentadienyl-[1,2-b]-phosphole)zirconium dichloride and methyl;

isopropylidenebis-6-(3-methylcyclopentadienyl-[1,2-b]-thiophene)zirconium dichloride and methyl;

isopropylidenebis-6-(3-isopropylcyclopentadienyl-[1,2-b]-thiophene)zirconium dichloride and methyl;

isopropylidenebis-6-(3-phenylcyclopentadienyl-[1,2-b]-thiophene)zirconium dichloride and methyl;

isopropylidenebis-6-(2,5-dimethyl-3-phenyl-cyclopentadienyl-[1,2-b]-thiophene)zirconium dichloride and methyl;

isopropylidenebis-6-[2,5-dimethyl-3-(2-methylphenyl)cyclopentadienyl-[1,2-b]-thiophene]zirconium dichloride and methyl;

isopropylidenebis-6-[2,5-dimethyl-3-(2,4,6-trimethylphenyl)cyclopentadienyl-[1,2-b]-thiophene]zirconium dichloride and methyl;

isopropylidenebis-6-[2,5-dimethyl-3-mesitylene-cyclopentadienyl-[1,2-b]-thiophene]zirconium dichloride and methyl;

isopropylidenebis-6-(2,4,5-trimethyl-3-phenyl-cyclopentadienyl-[1,2-b]-thiophene)zirconium dichloride and methyl;

isopropylidenebis-6-(2,5-diethyl-3-phenylcyclopentadienyl-[1,2-b]-thiophene)zirconium dichloride and methyl;

isopropylidenebis-6-(2,5-diisopropyl-3-phenyl-cyclopentadienyl-[1,2-b]-thiophene)zirconium dichloride and methyl;

isopropylidenebis-6-(2,5-diter-butyl-3-phenyl-cyclopentadienyl-[1,2-b]-thiophene)zirconium dichloride and methyl;

isopropylidenebis-6-(2,5-ditrimethylsilyl-3-phenylcyclopentadienyl-[1,2-b]-thiophene)zirconium dichloride and methyl;

isopropylidenebis-6-(3-methylcyclopentadienyl-[1,2-b]-silole)zirconium dichloride and methyl;

isopropylidenebis-6-(3-isopropylcyclopentadienyl-[1,2-b]-silole)zirconium dichloride and methyl;

isopropylidenebis-6-(3-phenylcyclopentadienyl-[1,2-b]-silole)zirconium dichloride and methyl;

isopropylidenebis-6-(2,5-dimethyl-3-phenylcyclopentadienyl-[1,2-b]-silole)zirconium dichloride and methyl;

isopropylidenebis-6-[2,5-dimethyl-3-(2-methylphenyl)cyclopentadienyl-[1,2-b]-silole]zirconium dichloride and methyl;

isopropylidenebis-6-[2,5-dimethyl-3-(2,4,6-trimethylphenyl)cyclopentadienyl-[1,2-b]-silole]zirconium dichloride and methyl;

isopropylidenebis-6-[2,5-dimethyl-3-mesitylenecyclopentadienyl-[1,2-b]-silole]zirconium dichloride and methyl;

isopropylidenebis-6-(2,4,5-trimethyl-3-phenyl-cyclopentadienyl-[1,2-b]-silole)zirconium dichloride and methyl;

isopropylidenebis-6-(2,5-diethyl-3-phenylcyclopentadienyl-[1,2-b]-silole)zirconium dichloride and methyl;

isopropylidenebis-6-(2,5-diisopropyl-3-phenyl-cyclopentadienyl-[1,2-b]-silole)zirconium dichloride and methyl;

isopropylidenebis-6-(2,5-diter-butyl-3-phenyl-cyclopentadienyl-[1,2-b]-silole)zirconium dichloride and methyl;

isopropylidenebis-6-(2,5-ditrimethylsilyl-3-phenylcyclopentadienyl-[1,2-b]-silole)zirconium dichloride and methyl;

isopropylidenebis-6-(3-methylcyclopentadienyl-[1,2-b]-tellurophene)zirconium dichloride and methyl;

isopropylidenebis-6-(3-isopropylcyclopentadienyl-[1,2-b]-tellurophene)zirconium dichloride and methyl;

isopropylidenebis-6-(3-phenylcyclopentadienyl-[1,2-b]-tellurophene)zirconium dichloride and methyl;

isopropylidenebis-6-(2,5-dimethyl-3-phenyl-cyclopentadienyl-[1,2-b]-tellurophene)zirconium dichloride and methyl;

isopropylidenebis-6-[2,5-dimethyl-3-(2-methylphenyl)cyclopentadienyl-[1,2-b]-tellurophene]zirconium dichloride and methyl;

isopropylidenebis-6-[2,5-dimethyl-3-(2,4,6-trimethylphenyl)cyclopentadienyl-[1,2-b]-tellurophene]zirconium dichloride and methyl;

isopropylidenebis-6-[2,5-dimethyl-3-mesitylene-cyclopentadienyl-[1,2-b]-tellurophene]zirconium dichloride and methyl;

isopropylidenebis-6-(2,4,5-trimethyl-3-phenyl-cyclopentadienyl-[1,2-b]-tellurophene)zirconium dichloride and methyl;

isopropylidenebis-6-(2,5-diethyl-3-phenylcyclopentadienyl-[1,2-b]-tellurophene)zirconium dichloride and methyl;

isopropylidenebis-6-(2,5-diisopropyl-3-phenyl-cyclopentadienyl-[1,2-b]-tellurophene)zirconium dichloride and methyl;

isopropylidenebis-6-(2,5-diter-butyl-3-phenyl-cyclopentadienyl-[1,2-b]-tellurophene)zirconium dichloride and methyl;

isopropylidenebis-6-(2,5-ditrimethylsilyl-3-phenylcyclopentadienyl-[1,2-b]-tellurophene)zirconium dichloride and methyl;

isopropylidenebis-6-(3-methylcyclopentadienyl-[1,2-b]-phosphole)zirconium dichloride and methyl;

isopropylidenebis-6-(3-isopropylcyclopentadienyl-[1,2-b]-phosphole)zirconium dichloride and methyl;

isopropylidenebis-6-(3-phenylcyclopentadienyl-[1,2-b]-phosphole)zirconium dichloride and methyl;

isopropylidenebis-6-(2,5-dimethyl-3-phenylcyclopentadienyl-[1,2-b]-phosphole)zirconium dichloride and methyl;

isopropylidenebis-6-[2,5-dimethyl-3-(2-methylphenyl)cyclopentadienyl-[1,2-b]-phosphole]zirconium dichloride and methyl;

isopropylidenebis-6-[2,5-dimethyl-3-(2,4,6-trimethylphenyl)cyclopentadienyl-[1,2-b]-phosphole]zirconium dichloride and methyl;

isopropylidenebis-6-[2,5-dimethyl-3-mesitylenecyclopentadienyl-[1,2-b]-phosphole]zirconium dichloride and methyl;

isopropylidenebis-6-(2,4,5-trimethyl-3-phenylcyclopentadienyl-[1,2-b]-phosphole)zirconium dichloride and methyl;

isopropylidenebis-6-(2,5-diethyl-3-phenylcyclopentadienyl-[1,2-b]-phosphole)zirconium dichloride and methyl;

isopropylidenebis-6-(2,5-diisopropyl-3-phenylcyclopentadienyl-[1,2-b]-phosphole)zirconium dichloride and methyl;

isopropylidenebis-6-(2,5-diter-butyl-3-phenylcyclopentadienyl-[1,2-b]-phosphole)zirconium dichloride and methyl;

isopropylidenebis-6-(2,5-ditrimethylsilyl-3-phenylcyclopentadienyl-[1,2-b]-phosphole)zirconium dichloride and methyl;

dimethylsilandiylbis-5-(2-methylcyclopentadienyl-[c]-thiophene)zirconium dichloride and methyl;

dimethylsilandiylbis-5-(2-isopropylcyclopentadienyl-[c]-thiophene)zirconium dichloride and methyl;

dimethylsilandiylbis-5-(2-phenylcyclopentadienyl-[c]-thiophene)zirconium dichloride and methyl;

dimethylsilandiylbis-5-(2,4-methyl-cyclopentadienyl-[c]-thiophene)zirconium dichloride and methyl;

dimethylsilandiylbis-5-[(2-methylphenyl)methylcyclopentadienyl-[c]-thiophene]zirconium dichloride and methyl;

dimethylsilandiylbis-5-[2-(2,4,6-trimethylphenyl)cyclopentadienyl-[c]-thiophene]zirconium dichloride and methyl;

dimethylsilandiylbis-5-[2-mesitylene-4-methylcyclopentadienyl-[c]-thiophene]zirconium dichloride and methyl;

dimethylsilandiylbis-5-(2,4-diisopropyl-cyclopentadienyl-[c]-thiophene)zirconium dichloride and methyl;

dimethylsilandiylbis-5-(2,4-diter-butyl-cyclopentadienyl-[c]-thiophene)zirconium dichloride and methyl;

dimethylsilandiylbis-5-(2,4-ditrimethylsilyl-cyclopentadienyl-[c]-thiophene)zirconium dichloride and methyl;

dimethylsilandiylbis-5-(2-methylcyclopentadienyl-[c]-phosphole)zirconium dichloride and methyl;

dimethylsilandiylbis-5-(2-isopropylcyclopentadienyl-[c]-phosphole)zirconium dichloride and methyl;

dimethylsilandiylbis-5-(2-phenylcyclopentadienyl-[c]-phosphole)zirconium dichloride and methyl;

dimethylsilandiylbis-5-(2,4-dimethyl-cyclopentadienyl-[c]-phosphole)zirconium dichloride and methyl;

dimethylsilandiylbis-5-[(2-methylphenyl)-4-methylcyclopentadienyl-[c]-phosphole]zirconium dichloride and methyl;

dimethylsilandiylbis-5-[2-(2,4,6-trimethylphenyl)cyclopentadienyl-[c]-phosphole]zirconium dichloride and methyl;

dimethylsilandiylbis-5-[2-mesitylene-4-methylcyclopentadienyl-[c]-phosphole]zirconium dichloride and methyl;

dimethylsilandiylbis-5-(2,4-diisopropyl-cyclopentadienyl-[c]-phosphole)zirconium dichloride and methyl;

dimethylsilandiylbis-5-(2,4-diter-butyl-cyclopentadienyl-[c]-phosphole)zirconium dichloride and methyl;

dimethylsilandiylbis-5-(2,4-ditrimethylsilyl-cyclopentadienyl-[c]-phosphole)zirconium dichloride and methyl;

dimethylsilandiylbis-5-(2-methylcyclopentadienyl-[c]-tellurophene)zirconium dichloride and methyl;

dimethylsilandiylbis-5-(2-isopropylcyclopentadienyl-[c]-tellurophene)zirconium dichloride and methyl;

dimethylsilandiylbis-5-(2-phenylcyclopentadienyl-[c]-tellurophene)zirconium dichloride and methyl;

dimethylsilandiylbis-5-(2,4-dimethyl-cyclopentadienyl-[c]-tellurophene)zirconium dichloride and methyl;

dimethylsilandiylbis-5-[(2-methylphenyl)-4-methylcyclopentadienyl-[c]-tellurophene]zirconium dichloride and methyl;

dimethylsilandiylbis-5-[2-(2,4,6-trimethylphenyl)cyclopentadienyl-[c]-tellurophene]zirconium dichloride and methyl;

dimethylsilandiylbis-5-[2-mesitylenemethylcyclopentadienyl-[c]-tellurophene]zirconium dichloride and methyl;

dimethylsilandiylbis-5-(2,4-diisopropyl-cyclopentadienyl-[c]-tellurophene)zirconium dichloride and methyl;

dimethylsilandiylbis-5-(2,4-diter-butyl-cyclopentadienyl-[c]-tellurophene)zirconium dichloride and methyl;

dimethylsilyl-5-(2,4-dimethyl-cyclopentadienyl-[c]-tellurophene)-1-(2-methyl-4-phenylindenyl)zirconium dichloride and methyl;

dimethylsilandiylbis-5-(2,4-ditrimethylsilyl-cyclopentadienyl-[c]-tellurophene)zirconium dichloride and methyl;

methylenebis-5-(2-methylcyclopentadienyl-[c]-thiophene)zirconium dichloride and methyl;

methylenebis-5-(2-isopropylcyclopentadienyl-[c]-thiophene)zirconium dichloride and methyl;

methylenebis-5-(2-phenylcyclopentadienyl-[c]-thiophene)zirconium dichloride and methyl;

methylenebis-5-(2,4-dimethyl-cyclopentadienyl-[c]-thiophene)zirconium dichloride and methyl;

methylenebis-5-[(2-methylphenyl)-4-methylcyclopentadienyl-[c]-thiophene]zirconium dichloride and methyl;

methylenebis-5-[2-(2,4,6-trimethylphenyl)cyclopentadienyl-[c]-thiophene]zirconium dichloride and methyl;

methylenebis-5-[2-mesitylene-4-methylcyclopentadienyl-[c]-thiophene]zirconium dichloride and methyl;

methylenebis-5-[2,4-diisopropyl-cyclopentadienyl-[c]-thiophene)zirconium dichloride and methyl;

methylenebis-5-(2,4-diter-butyl-cyclopentadienyl-[c]-thiophene)zirconium dichloride and methyl;

methylenebis-5-(2,4-ditrimethylsilyl-cyclopentadienyl-[c]-thiophene)zirconium dichloride and methyl;

methylenebis-5-(2-methylcyclopentadienyl-[c]-phosphole)zirconium dichloride and methyl;

methylenebis-5(2-isopropylcyclopentadienyl-[c]-phosphole)zirconium dichloride and methyl;

methylenebis-5-(2-phenylcyclopentadienyl-[c]-phosphole)zirconium dichloride and methyl;

methylenebis-5-(2,4-dimethyl-cyclopentadienyl-[c]-phosphole)zirconium dichloride and methyl;

methylenebis-5-[(2-methylphenyl)-4-methylcyclopentadienyl-[c]-phosphole]zirconium dichloride and methyl;

methylenebis-5-[2-(2,4,6-trimethylphenyl)cyclopentadienyl-[c]-phosphole]zirconium dichloride and methyl;

methylenebis-5-[2-mesitylene-4-methylcyclopentadienyl-[c]-phosphole]zirconium dichloride and methyl;

methylenebis-5-(2,4-diisopropyl-cyclopentadienyl-[c]-phosphole)zirconium dichloride and methyl;

methylenebis-5-(2,4-diter-butyl-cyclopentadienyl-[c]-phosphole)zirconium dichloride and methyl;

methylenebis-5-(2,4-ditrimethylsilyl-cyclopentadienyl-[c]-phosphole)zirconium dichloride and methyl;

methylenebis-5-(2-methylcyclopentadienyl-[c]-tellurophene)zirconium dichloride and methyl;

methylenebis-5-(2-isopropylcyclopentadienyl-[c]-tellurophene)zirconium dichloride and methyl;

methylenebis-5-(2-phenylcyclopentadienyl-[c]-tellurophene)zirconium dichloride and methyl;

methylenebis-5-(2,4-dimethyl-cyclopentadienyl-[c]-tellurophene)zirconium dichloride and methyl;

methylenebis-5-[(2-methylphenyl)-4-methylcyclopentadienyl-[c]-tellurophene]zirconium dichloride and methyl;

methylenebis-5-[2-(2,4,6-trimethylphenyl)cyclopentadienyl-[c]-tellurophene]zirconium dichloride and methyl;

methylenebis-5-[2-mesitylene-4-methylcyclopentadienyl-[c]-tellurophene]zirconium dichloride and methyl;

methylenebis-5-(2,4-diisopropyl-cyclopentadienyl-[c]-tellurophene)zirconium dichloride and methyl;

methylenebis-5-(2,4-diter-butyl-cyclopentadienyl-[c]-tellurophene)zirconium dichloride and methyl;

dimethylsilyl-5-(2,4-dimethyl-cyclopentadienyl-[c]-tellurophene)-1-(2-methyl-4-phenylendenyl)zirconium dichloride and methyl;

methylenebis-5-(2,4-ditrimethylsilyl-cyclopentadienyl-[c]-tellurophene)zirconium dichloride and methyl;

dimethylsilandiylbis-4-(cyclopentadienyl-[2,1-b]-thiophene)zirconium dichloride and methyl;

dimethylsilandiylbis-4-(2-methylcyclopentadienyl-[2,1-b]-thiophene)zirconium dichloride and methyl;

dimethylsilandiylbis-4-(2,5-dimethylcyclopentadienyl-[2,1-b]-thiophene)zirconium dichloride and methyl;

dimethylsilandiylbis-4-(2,5-diisopropylcyclopentadienyl-[2,1-b]-thiophene)zirconium dichloride and methyl;

dimethylsilandiylbis-4-(2,5-diter-butylcyclopentadienyl-[2,1-b]-thiophenerzirconium dichloride and methyl;

dimethylsilandiylbis-4-(2,5-ditrimethylsilylcyclopentadienyl-[2,1-b]-thiophene)zirconium dichloride and methyl;

dimethylsilyl-4-(2,5-ditrimethylsilylcyclopentadienyl-[2,1-b]-thiophene)-1-(2-methyl-4-phenyl)zirconium dichloride and methyl;

dimethylsilandiylbis-4-(cyclopentadienyl-[2,1-b]-tellurophene)zirconium dichloride and methyl;

dimethylsilandiylbis-4-(2-methylcyclopentadienyl-[2,1-b]-tellurophene)zirconium dichloride and methyl;

dimethylsilandiylbis-4-(2,5-dimethylcyclopentadienyl-[2,1-b]-tellurophene)zirconium dichloride and methyl;

dimethylsilandiylbis-4-(2,5-diisopropylcyclopentadienyl-[2,1-b]-tellurophene)zirconium dichloride and methyl;

dimethylsilandiylbis-4-(2,5-diter-butylcyclopentadienyl-[2,1-b]-tellurophene)zirconium dichloride and methyl;

dimethylsilandiylbis-4-(2,5-ditrimethylsilylcyclopentadienyl-[2,1-b]-tellurophene)zirconium dichloride and methyl;

dimethylsilandiyl-6-(2,5-dimethyl-3-phenylcyclopentadienyl-[1,2-b]-thiophene)(3-methylcyclopentadienyl)zirconium dichloride and methyl;

dimethylsilandiyl-6-(2,5-dimethyl-3-phenylcyclopentadienyl-[1,2-b]-thiophene)(3-ter-butylcyclopentadienyl)zirconium dichloride and methyl;

dimethylsilandiyl-6-(2,5-dimethyl-3-phenylcyclopentadienyl-[1,2-b]-thiophene)-1-(2-methyl-4-phenylindenyl)zirconium dichloride and methyl;

dimethylsilandiyl-6-(2,5-dimethyl-3-phenylcyclopentadienyl-[1,2-b]-thiophene)-1-(benzoindenyl)zirconium dichloride and methyl;

dimethylsilandiyl-6-(2,5-dimethyl-3-phenylcyclopentadienyl-[1,2-b]-silole)-1-(2-methyl-4-phenylindenyl)zirconium dichloride and methyl;

dimethylsilandiyl-6-(2,5-dimethyl-3-phenylcyclopentadienyl-[1,2-b]-silole)-1-(benzoindenyl)zirconium dichloride and methyl;

dimethylsilandiyl-6-(2,5-dimethyl-3-phenylcyclopentadienyl-[1,2-b]-tellurophene)-1-(2-methyl-4-phenylindenyl)zirconium dichloride and methyl;

dimethylsilandiyl-6-(2,5-dimethyl-3-phenylcyclopentadienyl-[1,2-b]-thiophene)-1-(2-methyl-4-phenylindenyl)zirconium dichloride and methyl;

dimethylsilandiyl-6-(2,5-dimethyl-3-phenylcyclopentadienyl-[1,2-b]-silole)-1-(2-methyl-4-phenylindenyl)zirconium dichloride and methyl;

dimethylsilandiyl-6-(2,5-dimethyl-3-phenylcyclopentadienyl-[1,2-b]-tellurophene)-1-(2-methyl-4-phenylindenyl)zirconium dichloride and methyl;

dimethylsilandiyl-6-(2,5-dimethyl-3-phenylcyclopentadienyl-[1,2-b]-phosphole)-1-(2-methyl-4-phenylindenyl)zirconium dichloride and methyl;

dimethylsilandiyl-6-(2,5-dimethyl-3-phenylcyclopentadienyl-[1,2-b]-phosphole)-1-(benzoindenyl)zirconium dichloride and methyl;

dimethylsilandiyl-5-(2,4-dimethyl-cyclopentadienyl-[c]-thiophene)-1-(2-methyl-4-phenylindenyl)zirconium dichloride and methyl;

dimethylsilandiyl-5-(2,4-dimethyl-cyclopentadienyl-[c]-phosphole)-1-(2-methyl-4-phenylindenylzirconiun dichloride and methyl;

dimethylsilandiyl-5-(2,4-dimethyl-cyclopentadienyl-[c]-thiophene)-1-(2-methyl-4-phenylindenyl)zirconium dichloride and methyl;

dimethylsilandiyl-5-(2,4-dimethyl-cyclopentadienyl-[c]-phosphole)-1-(2-methyl-4-phenylindenyl)zirconium dichloride and methyl;

dimethylsilandiyl-5-(2,4-dimethyl-cyclopentadienyl-[c]-phosphole)-1-(benzoindenyl)zirconium dichloride and methyl;

dimethylsilandiyl-4-(2,5-ditrimethylsilylcyclopentadienyl-[2,1-b]-tellurophene)-1-(2-methyl-4-phenyl)zirconium dichloride and methyl.

An interesting class of metallocene compounds according to the present invention is that of formula (I) wherein both Y and Z are a moiety of formula (II), $R^1$ is a $C_1$–$C_{20}$-alkyl group, preferably a methyl group, $R^2$ is hydrogen, $R^3$ is different from hydrogen, B and D are carbon atoms, A is an element of the group 16 of the Periodic Table of the Elements (new IUPAC version), preferably sulfur, m is 0, n and s are 1. Preferably $R^3$ is a $C_6$–$C_{20}$-aryl group, such as a phenyl group or a naphthyl group, or a $C_7$–$C_{20}$-alkylaryl group wherein the alkyl group is ortho-substituted to the aryl substituent, such as an ortho-methylphenyl group or the aryl group is a 2,4 disubstituted phenyl group such as 2,4-dimethyl-phenyl. Preferably It is different from hydrogen. Preferably $R^5$ is a hydrogen.

In this class of metallocenes according to the invention the ring that comprises the heteroatom contains a double bond and thus has an aromatic character.

Non limiting examples of said class are:

dimethylsilandiylbis-6-(2,5-dimethyl-3-phenyl-cyclopentadienyl-[1,2-b]-thiophene)zirconium dichloride, dimethylsilandiylbis-6-(3,5-dimethyl-cyclopentadienyl-[1,2-b]-thiophene)zirconium dichloride and dimethylsilandiylbis-6-[2,5-dimethyl-3-(2'-methylphenylcyclopentadienyl-[1,2-b]-thiophene]zirconium dichloride.

Another particular advantageous class of metallocenes according to the present invention are those wherein both Y and Z are a moiety of formula (II), L is a $>C(R^{17})_2$ group, $R^1$ is a hydrogen atom, $R^2$ is different from hydrogen.

Non limiting examples of said class are:

isopropylidenebis-6-(4-methylcyclopentadienyl-[1,2-b]-thiophene)zirconium dichloride and methyl;

isopropylidenebis-6-(4-isopropylcyclopentadienyl-[1,2-b]-thiophene)zirconium dichloride and methyl;

isopropylidenebis-6-(4-terbutylcyclopentadienyl-[1,2-b]-thiophene)zirconium dichloride and methyl;

isopropylidenebis-6-(4-phenylclopentadienyl-[1,2-b]-thiophene)zirconium dichloride and methyl;

methylenebis-6-(4-methylcyclopentadienyl-[1,2-b]-thiophene)zirconium dichloride and methyl;

methylenebis-6-(4-isopropylcyclopentadienyl-[1,2-b]-thiophene)zirconium dichloride and methyl;

methylenebis-6-(4-terbutylcyclopentadienyl-[1,2-b]-thiophene)zirconium dichloride and methyl;

methylenebis-6-(4-phenylclopentadienyl-[1,2-b]-thiophene)zirconium dichloride and methyl.

Yet another particular advantageous class of metallocene compound according to the present invention corresponds to formula (I) wherein both Y and Z are a moiety of formula (II), m is 2 and $R^5$ is not hydrogen.

Non limiting examples of said class are:

dimethylsilandiylbis-6-(1,1,2,5-tetramethyl-3-phenylcyclopentadienyl-[1,2-b]-silole)zirconium dichloride and methyl;

dimethylsilandiylbis-6-(1,1,2,5-tetramethyl-3-phenylcyclopentadienyl-[1,2-b]-cyclopentadien)zirconium dichloride and methyl;

isopropylidenebis-6-(1,1,2,5-tetramethyl-3-phenylcyclopentadienyl-[1,2-b]-silole)zirconium dichloride and methyl;

isopropylidenebis-6-(1,1,2,5-tetramethyl-3-phenylcyclopentadienyl[1,2-b]-cyclopentadien) zirconium dichloride and methyl.

According to another aspect of the present invention it is provided a class of ligands of formula (V):

(V)

wherein Y' is a moiety of formula (VI):

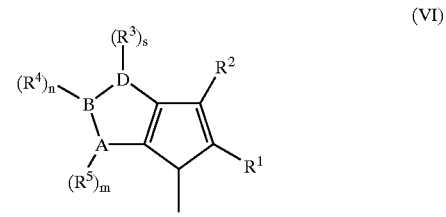

(VI)

wherein $R^1$, $R^2$, $R^3$, $R^4$, $R^5$, A, B, D, n, m and s are defined as described above and the ring containing A, B and D can have double bonds in any of the allowed positions, having an aromatic character; and/or its double bond isomers;

Z' is selected from a moiety of formula (VI) and from a moiety of formula (VII):

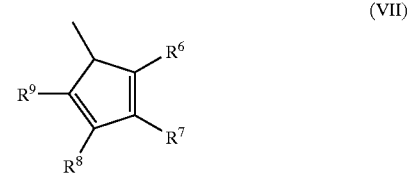

(VII)

and/or its double bond isomers;

$R^6$, $R^7$, $R^8$ and $R^9$ are defined as described above;

when Z' is equal to Y', A, B and D in Y' and Z' can be the same or different from each other;

L is a divalent bridge as defined above.

Preferably Z' is equal to Y'; $R^1$ is a $C_1$–$C_{20}$-alkyl group, preferably a methyl group, $R^2$ is hydrogen, $R^3$ is different from hydrogen, B and D are carbon atoms, A is an element of the group 16 of the Periodic Table of the Elements (new IUPAC version), preferably sulfur, m is 0, n and s are 1.

More preferably $R^3$ is a $C_6$–$C_{20}$-aryl group, such as a phenyl group or a naphthyl group, or a $C_7$–$C_{20}$-alkylaryl group wherein the alkyl group is ortho-substituted or ortho and meta-substituted to the aryl substituent, such as an ortho-methylphenyl group or 2–4 methylphenyl group. Preferably $R^4$ is different from hydrogen. Preferably $R^5$ is a hydrogen.

When Z' is different from Y' it is preferred a moiety of formula (VIII):

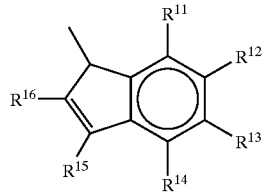

(VIII)

and/or its double bond isomers;

wherein $R^{11}$, $R^{12}$, $R^{13}$, $R^{14}$, $R^{15}$ and $R^{16}$ are defined as above.

Non limiting examples of said class are:

dimethylbis-6-(3-methylcyclopentadienyl-[1,2-b]-thiophene)silane;
dimethylbis-6-(3-isopropylcyclopentadienyl-[1,2-b]-thiophene)silane;
dimethylbis-6-(3-phenylcyclopentadienyl-[1,2-b]-thiophene)silane;
dimethylbis-6-(2,5-dimethyl-3-phenylcyclopentadienyl-[1,2-b]-thiophene]silane;
dimethylbis-6-[2,5-dimethyl-3-(2-methylpheny)cyclopentadienyl-[1,2-b]-thiophene]silane;
dimethylbis-6-[2,5-dimethyl-3-(2,4,6-trimethylphenyl)cyclopentadienyl-[1,2-b]-thiophene]silane;
dimethylbis-6-[2,5-dimethyl-3-mesitylenecyclopentadienyl-[1,2-b]-thiophene]silane;
dimethylbis-6-(2,4,5-trimethyl-3-phenylcyclopentadienyl-[1,2-b-]-thiophene)silane;
dimethylbis-6-(2,5-diethyl-3-phenylcyclopentadienyl-[1,2-b]-thiophene)silane;
dimethylbis-6-(2,5-diisopropyl-3-phenylcyclopentadienyl-[1,2-b]-thiophene)silane;
dimethylbis-6-(2,5-diter-butyl-3-phenylcyclopentadienyl-[1,2-b]-thiophene)silane;
dimethylbis-6-(2,5-ditrimethylsilyl-3-phenylcyclopentadienyl-[1,2-b]-thiophene)silane;
dimethylbis-6-(3-methylcyclopentadienyl-[1,2-b]-silole)silane;
dimethylbis-6-(3-isopropylcyclopentadienyl-[1,2-b]-silole)silane;
dimethylbis-6-(3-phenylcyclopentadienyl-[1,2-b]-silole)silane;
dimethylbis-6-(2,5-dimethyl-3-phenylcyclopentadienyl-[1,2-b]-silolesilane;
dimethylbis-6-[2,5-dimethyl-3-(2-methylphenyl)cyclopentadienyl-[1,2-b]-silole]silane;
dimethylbis-6-[2,5-dimethyl-3-(2,4,6-trimethylphenyl)cyclopentadienyl-[1,2-b]-silole]silane;
dimethylbis-6-[2,5-dimethyl-3-mesitylenecyclopentadienyl-[1,2-b-silole]silane;
dimethylbis-6-(2,4,5-trimethyl-3-phenylcyclopentadienyl-[1,2-b]-silole)silane;
dimethylbis-6-(2,5-diethyl-3-phenylcyclopentadienyl-[1,2-b]-silole)silane;
dimethylbis-6-(2,5-diisopropyl-3-phenylcyclopentadienyl-[1,2-b]-silole)silane;
dimethylbis-6-(2,5-diter-butyl-3-phenylcyclopentadienyl-[1,2-b]-silole)silane;
dimethylsilyl-6-(2,5-dimethyl-3-phenylcyclopentadienyl-[1,2-b]-silole)-1-(2-methyl-4-phenylindenyl)silane;
dimethylbis-6-(2,5-ditrimethylsilyl-3-phenylcyclopentadienyl-[1,2-b]-silole)silane;
dimethylbis-6-(3-methylcyclopentadienyl-[1,2-b]-tellurophene)silane;
dimethylbis-6-(3-isopropylcyclopentadienyl-[1,2-b]-tellurophene)silane;
dimethylbis-6-(3-phenylcyclopentadienyl-[1,2-b]-tellurophene)silane;
dimethylbis-6-(2,5-dimethyl-3-phenylcyclopentadienyl-[1,2-b]-tellurophene)silane;
dimethylbis-6-[2,5-dimethyl-3-(2-methylphenyl)cyclopentadienyl-[1,2-b]-tellurophene]silane;
dimethylbis-6-[2,5-dimethyl-3-(2,4,6-trimethylphenyl)cyclopentadienyl-[1,2-b]-tellurophene]silane;
dimethylbis-6-[2,5-dimethyl-3-mesitylenecyclopentadienyl-[1,2-b]-tellurophene]silane;
dimethylbis-6-(2,4,5-trimethyl-3-phenylcyclopentadienyl-[1,2-b]-tellurophene)silane;
dimethylbis-6-(2,5-diethyl-3-phenylcyclopentadienyl-[1,2-b]-tellurophene)silane;
dimethylbis-6-(2,5-diisopropyl-3-phenylcyclopentadienyl-[1,2-b]-tellurophene)silane; 1dimethylbis-6-(2,5-diter-butyl-3-phenylcyclopentadienyl-[1,2-b]-tellurophene)silane;
dimethylsilyl-6-(2,5-dimethyl-3-phenylcyclopentadienyl-[1,2-b]-tellurophene)-1-(2-methyl-4-phenylindenyl)silane;
dimethylbis-6-(2,5-ditrimethylsilyl-3-phenylcyclopentadienyl-[1,2-b]-tellurophene)silane;
dimethylbis-6-(3-methylcyclopentadienyl-[1,2-b]-phosphole)silane;

dimethylbis-6-(3-isopropylcyclopentadienyl-[1,2-b]-phosphole)silane;
dimethylbis-6-(3-phenylcyclopentadienyl-[1,2-b]-phosphole)silane;
dimethylbis-6-(2,5-dimethyl-3-phenylcyclopentadienyl-[1,2-b]-phosphole)silane;
dimethylbis-6-[2,5-dimethyl-3-(2-methylphenyl)cyclopentadienyl-[1,2-b]-phosphole]silane;
dimethylbis-6-[2,5-dimethyl-3-(2,4,6-trimethylphenyl)cyclopentadienyl-[1,2-b]-phosphole]silane;
dimethylbis-6-[2,5-dimethyl-3-mesitylenecyclopentadienyl-[1,2-b]-phosphole]silane;
dimethylbis-6-(2,4,5-trimethyl-3-phenylcyclopentadienyl-[1,2-b]-phosphole)silane;
dimethylbis-6-(2,5-diethyl-3-phenylcyclopentadienyl-[1,2-b]-phosphole)silane;
dimethylbis-6-(2,5-diisopropyl-3-phenylcyclopentadienyl-[1,2-b]-phosphole)silane;
dimethylbis-6-(2,5-diter-butyl-3-phenylcyclopentadienyl-[1,2-b]-phosphole)silane;
dimethylbis-6-(2,5-ditrimethylsilyl-3-phenylcyclopentadienyl-[1,2-b]-phosphole)silane;
dimethylsilandiyl-6-(2,5-dimethyl-3-phenylcyclopentadienyl-[1,2-b]-thiophene)-1-(2-methyl-4-phenylindenyl)silane;
dimethylsilandiyl-6-(2,5-dimethyl-3-phenylcyclopentadienyl-[1,2-b]-phosphole)-1-(2-methyl-4-phenylindeneylsilane;
dimethylsilandiyl-6-(2,5-dimethyl-3-phenylcyclopentadienyl-[1,2-b]-tellurophene)-1-(2-methyl-4-phenylindenyl)silane.

Most preferably the ligands according to the present invention are
dimethylbis-6-(2,5-dimethyl-3-phenylcyclopentadienyl-[1,2-b]-thiophene)silane;
dimethylbis-6-[2,5-dimethyl-3-(2'-methylphenyl)cyclopentadienyl-[1,2-b]-thiophene]silane;
dimethylbis-6-(3,5-dimethylcyclopentadienyl-[1,2-b]-thiophene)silane.

The aforementioned compounds of formula (V) are particularly useful as intermediate ligands for the preparation of the metallocene compounds of formula (I).

According to a further aspect of the present invention there is provided a process for the preparation of a ligand of formula (V), wherein L, Y' and Z' are defined as described above, with the proviso that $R^2$ is a hydrogen and D is a carbon atom, comprising the following steps:
a) contacting a compound of formula (IX)

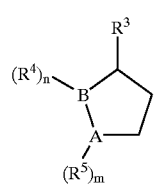
(IX)

wherein the double bonds can be in any of the allowed positions;
A, B, $R^3$, $R^4$, $R^5$, n and m have the meaning as defined above, with a compound of general formula (X):

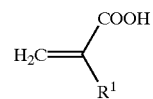
(X)

wherein $R^1$ has the same meaning as defined above;
In the presence of a ring-closure agent, to obtain the compound of the general formula (XI):

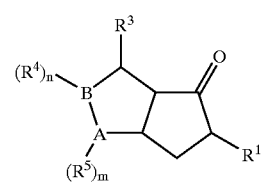
(XI)

wherein the double bonds can be in any of the allowed positions;
b) conversion into the compound of formula (XII):

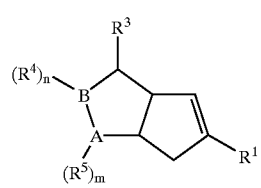
(XII)

wherein the double bonds can be in any of the allowed positions; and
when Z' is equal to Y', wherein A and B in Y' and Z' are the same or different from each other:
c1) treating the compound of formula (XII) with a base selected from hydroxides and hydrides of alkali- and earth-alkali metals, metallic sodium and potassium, and organometallic lithium salts, and subsequently contacting with a compound of formula $LQ_2$ (XIII), wherein L has the same meaning as defined above, and Q is an halogen atom selected from chloride, iodide and bromide preferably bromine, wherein the molar ratio between the compound of formulae (XII) and (XIII) is at least 2;
or when Z' is a compound of formula (VII):
c2) treating the compound of formula (XII) with a base as defined under c1), and subsequently contacting with a compound of formula Z'LQ (XIV), wherein L has the same meaning as defined above, and Q is a halogen atom selected from chloride, iodide and bromide;

Preferably in the process according to the present invention the ring-closing agent is selected from phosphorus pentoxide-methansulfonic acid (PPMA) and polyphosphoric acid (PPA).

In the process according to the present invention the compound of general formula (X) is selected from α,β-unsaturated acids. Most preferably methacrylic acid is used.

Preferably, in the process according to the present invention the compound of general formula (IX) is 1-methyl-3-bromo-thiophene.

In the process according to the present invention the conversion into the compound of formula (XII) preferably is carried out in the presence of a reduction agent and para-toulene sulfonic acid monohydrate.

In the process according to the present invention the reduction agent is preferably lithium aluminum hydride (LiAlH$_4$).

Non-limiting examples of compounds of formula LQ$_2$ (XIII) are dimethyldichlorosilane, diphenyldichlorosilane, dimethyldichlorogermanium, 2,2-dichloropropane and 1,2-dibromoethane.

Preferably, in the process according to the present invention the compound of formula LQ$_2$ (XIII) is dimethyldichlorosilane.

Non-limiting examples of compounds able to form the anionic compound of formula (XII) are hydroxides and hydrides of alkali- and earth-alkali metals, metallic sodium and potassium, and organometallic lithium salts. Preferably butyllithium is used.

Non-limiting examples of coupling agent used in step a) are Ni, Pd or Pt-based coupling agent. Coupling agents of this kind which are generally used are described in "Comprehensive organic synthesis", Eds. B. M. Trost and I. Fleming, Pergamon, Oxford (1991), Vol. 3, Part 1.6, p.241. Preferably bis(diphenylphosphino)propane)] dichloronickel(II) (Ni(dPPP)) is used.

The synthesis of the above bridged ligands is preferably carried out by adding a solution of an organic lithium compound in an apolar solvent to a solution of the compound (XII) in an aprotic polar solvent. The thus obtained solution containing the compound (XII) in the anionic form is then added to a solution of the compound of formula LQ$_2$ (XIII) in an aprotic polar solvent. The bridged ligand can be finally separated by conventional general known procedures.

Not limitative examples of aprotic polar solvents which can be used in the above process are tetrahydrofurane, dimethoxyethane, diethylether, toluene and dichloromethane. Not limitative examples of apolar solvents suitable for the above process are pentane, hexane and benzene.

During the whole process, the temperature is preferably kept between −180° C. and 80° C., and more preferably between −20° C. and 40° C.

A still further aspect of the present invention is a process for the preparation of the metallocene compounds of formula (I), obtainable by contacting a ligand of formula (V) as described above, with a compound capable of forming a corresponding dianionic compound thereof and thereafter with a compound of formula MX$_{p+2}$, wherein M, X and p have the meanings as defined above.

The compound able to form said dianion is selected from the group consisting of hydroxides and hydrides of alkali- and earth-alkali metals, metallic sodium and potassium, and organometallic lithium salts, and preferably said anion is n-butyllithium.

Non-limiting examples of compounds of formula MX$_{p+2}$ are titanium tetrachloride, zirconium tetrachloride and hafnium tetrachloride.

More specifically, said bridged ligands are dissolved in an aprotic polar solvent and to the obtained solution is added a solution of an organic lithium compound in an apolar solvent The thus obtained anionic form is separated, dissolved in an aprotic polar solvent and thereafter added to a suspension of the compound MX$_{p+2}$ in an aprotic polar solvent. At the end of the reaction, the solid product obtained is separated from the reaction mixture by techniques commonly used in the state of the art.

Non limiting examples of aprotic polar solvents suitable for the above reported processes are tetrahydrofurane, dimethoxyethane, diethylether, toluene and dichloromethane. Non limiting examples of apolar solvents suitable for the above process are pentane, hexane and benzene.

During the whole process, the temperature is preferably kept between −180° C. and 80° C., and more preferably between −20° C. and 40° C.

When at least one X substituent in the metallocene compound of formula (I) is different from halogen, it is necessary to substitute at least one substituent X in the obtained metallocene with at least another substituent different from halogen. Such a substitution reaction is carried out by methods known in the state of the art. For example, when the substituents X are alkyl groups, the metallocenes can be reacted with alkylmagnesium halides (Grignard reagents) or with lithiumalkyl compounds.

During the whole process, the temperature is preferably kept between −180° C. and 80° C., and more preferably between −20° C. and 40° C.

The heterocyclic metallocene compounds of the present invention can conveniently be used as catalyst components for the polymerization of olefins.

Thus, according to a still further aspect of the present invention there is provided a catalyst for the polymerization of olefins, obtainable by contacting:

A) a metallocene compound of formula (I), and

B) an alumoxane and/or a compound capable of forming an alkyl metallocene cation.

The alumoxane used as component (B) can be obtained by reacting water with an organo-aluminum compound of formula H$_j$AlR$^{18}_{3-j}$ or H$_j$AlR$^{18}_{6-j}$, where R$^{18}$ substituents, same or different, are hydrogen atoms, C$_1$–C$_{20}$-alkyl, C$_3$–C$_{20}$-cycloalkyl, C$_6$–C$_{20}$-aryl, C$_7$–C$_{20}$-alkylaryl or C$_7$–C$_{20}$-arylalkyl, optionally containing silicon or germanium atoms with the proviso that at least one R$^{18}$ is different from halogen, and J ranges from 0 to 1, being also a non-integer number. In this reaction the molar ratio of Al/water is preferably comprised between 1:1 and 100:1.

Preferably the molar ratio between aluminum and the metal of the metallocene is comprised between about 10:1 and about 20000:1, and more preferably between about 100:1 and about 5000:1. Higher aluminum/zirconium molar ratio can be used with good results even if not practical on industrial scale. The alumoxanes used in the catalyst according to the invention are considered to be linear, branched or cyclic compounds containing at least one group of the type:

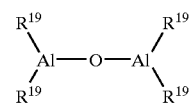

wherein the R$^{19}$ substituents, same or different, are hydrogen atoms, C$_1$–C$_{20}$-alkyl, C$_3$–C$_{20}$-cycloalkyl, C$_6$–C$_{20}$-aryl, C$_7$–C$_{20}$-alkylaryl or C$_7$–C$_{20}$-arylalkyl, optionally containing silicon or germanium atoms, or are a —O—Al(R$^{19}$)$_2$ group and, if appropriate, some R$^{19}$ substituents can be halogen atoms.

In particular, alumoxanes of the formula:

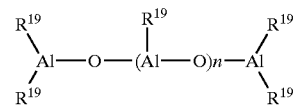

can be used in the case of linear compounds, wherein n is 0 or an integer from 1 to 40 and the R$^{19}$ substituents are defined as above, or alumoxanes of the formula:

can be used in the case of cyclic compounds, wherein n is an integer from 2 to 40 and the $R^6$ substituents are defined as above.

Examples of alumoxanes suitable for use according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl) alumoxane (TDMBAO), tetra-(2,3,3-trimethylbutyl) alumoxane (TIMBAO), Other interesting alumoxanes are those obtainable by contacting water with an organoaluminum compound described in the international application PCT/EP00/09111 such as tris(2-phenyl-propyl)aluminium, tris[2-(4-fluoro-phenyl)-propyl]aluminium, tris[2-(4-chlorophenyl)-propyl] aluminium, tris[2-(3-isopropyl-phenyl)-propyl]aluminium, tris(2-phenyl-butyl)aluminium, tris(3-methyl-2-phenyl-butyl)aluminium, tris(2-phenyl-pentyl)aluminium, tris[2-(pentafluorophenyl)-propyl]aluminium, tris[2,2-diphenyl-ethyl]aluminium and tris[2-phenyl-2-methyl-propyl] aluminium.

Further particularly interesting cocatalysts are those described in WO 99/21899 in which the alkyl groups have specific branched patterns.

Non-limiting examples of aluminum compounds according to said PCT application are:

tris(2,3,3-trimethyl-butyl)aluminum, tris(2,3-dimethyl-hexyl)aluminum, tris(2,3-dimethyl-butyl)aluminum, tris(2,3-dimethyl-pentyl)aluminum, tris(2,3-dimethyl-heptyl)aluminum, tris(2-methyl-3-ethyl-pentyl) aluminum, tris(2-methyl-3-ethyl-hexyl)aluminum, tris (2-methyl-3-ethyl-heptyl)aluminum, tris(2-methyl-3-propyl-hexyl)aluminum, tris(2-ethyl-3-methyl-butyl) aluminum, tris(2-ethyl-3-methyl-pentyl)aluminum, tris (2,3-diethyl-pentyl)aluminum, tris(2-propyl-3-methyl-butyl)aluminum, tris(2-isopropyl-3-methyl-butyl) aluminum, tris(2-isobutyl-3-methyl-pentyl)aluminum, tris(2,3,3-trimethyl-pentyl)aluminum, tris(2,3,3-trimethyl-hexyl)aluminum, tris(2-ethyl-3,3-dimethyl-butyl)aluminum, tris(2-ethyl-3,3-dimethyl-pentyl) aluminum, tris(2-isopropyl-3,3-dimethyl-butyl) aluminum, tris(2-trimethylsilyl-propyl)aluminum, tris (2-methyl-3-phenyl-butyl)aluminum, tris(2-ethyl-3-phenyl-butyl)aluminum, tris(2,3-dimethyl-3-phenyl-butyl)aluminum, as well as the corresponding compounds wherein one of the hydrocarbyl groups is replaced by an hydrogen atom, and those wherein one or two of the hydrocarbyl groups are replaced by an isobutyl group.

Other interesting aluminum compounds are compounds wherein $R^{18}$ contains an aryl group such as:

tris(2-phenyl-propyl)aluminium, tris[2-(4-fluoro-phenyl)-propyl]aluminium, tris[2-(4-chloro-phenyl)-propyl] aluminium, tris[2-(3-isopropyl-phenyl)-propyl] aluminium, tris(2-phenyl-butyl)aluminium, tris(3-methyl-2-phenyl-butyl)aluminium, tris(2-phenyl-pentyl)aluminium, tris[2-(pentafluorophenyl)-propyl] aluminium, tris[2,2-diphenyl-ethyl]aluminium and tris [2-phenyl-2-methyl-propyl]aluminium.

Amongst the above aluminum compounds, trimethylaluminium (TMA), triisobutylaluminium (TIBAL), tris(2,4,4-trimethyl-pentyl)aluminum (TIOA), tris(2,3-dimethylbutyl) aluminum (TDMBA) and tris(2,3,3-trimethylbutyl) aluminum (TTMBA) tris(2-phenyl-propyl)aluminium (TPPA), tris[2-(4-fluoro-phenyl)propyl]aluminium (TFPPA) are preferred.

Non limitative examples of compounds able to form a metallocene alkyl cation are compounds of formula $D^+E^-$, wherein $D^+$ is a Brønsted acid, able to give a proton and to react irreversibly with a substituent X of the metallocene of formula (I) and $E^-$ is a compatible anion, which is able to stabilize the active catalytic species originating from the reaction of the two compounds, and which is sufficiently labile to be able to be removed by an olefinic monomer. Preferably, the anion $V^-$ comprises one or more boron atoms. More preferably, the anion $V^-$ is an anion of the formula $BAr^{(-)}_4$, wherein substituents Ar, the same or different from each other, are aryl radicals such as phenyl, pentafluorophenyl, bis(trifluoromethyl)phenyl. Particularly preferred is the tetrakis-pentafluorophenyl borate. Furthermore, compounds of formula $BAr_3$ can be suitably used wherein Ar is a $C_7$–$C_{20}$ aryl group optionally substituted with heteroatoms.

The catalysts used in the process of the present invention can be also used on inert supports. This is obtained by depositing the metallocene (A), or the product of the reaction of the same with the component (B), or the component (B) and thereafter the metallocene (A), on supports such as for example silica, alumina, styrene-divinylbenzene copolymers, polyethylene or polypropylene.

The solid compound so obtained, in combination with further addition of the alkyl aluminum compound as such or pre-reacted with water, is usefully employed in gas phase polymerisation. Catalysts of the present invention are useful in the homo- and copolymerization reaction of olefins. Therefore, a still further object of the present invention is a process for the polymerization of one or more olefins comprising the polymerization reaction of one or more olefinic monomer in the presence of a catalyst as above described.

The catalysts of the present invention can be used in the homo-polymerisation reaction of olefins, such as ethylene for the preparation of HDPE, or of alpha-olefins, such as propylene and 1-butene. Particular interesting results are achieved in the polymerisation of propylene carried out in the presence of the above-described catalyst containing the metallocene of the present invention.

It has been found that when the polymerization of propylene is carried out in the presence of the metallocene compounds of the present, the molecular weight of the obtained propylene polymers are unexpectedly high. The intrinsic viscosity (I.V.) of the obtained polypropylene is generally higher than 0.5 dL/g preferably 1 dL/g and can reach values as high as 5 dL/g or even higher.

The obtained propylene polymers are characterized by high isotacticity values. Thus the amount of sequences mrrm (in mol %) is extremely low. In generally the amount of sequences mrrm (in mol %) is lower than 1, preferably lower than 0.5.

When the polymerization of propylene is carried out in the presence of the metallocene compounds of the present invention the melting point of the obtained polypropylene is considerably high. In generally the melting point of the obtained polypropylene is higher than 145° C. and can reach values of 160° C. or even higher.

Particularly interesting results are obtained when the catalyst of the present invention, in particular when both Y and Z belong to formula (II) and $R^3$ is $C_6$–$C_{20}$ aryl $C_7$–$C_{20}$ alkyl aryl or $C_7$–$C_{20}$ arylalkyl, is used in conjunction with compounds able to form a metallocene alkyl cation of formula $T^+V^-$ wherein T and V are described above. With these cocatalyst is possible to obtain highly isospecific polymers with very low regio-error contents.

A still further advantageous characteristic of the metallocenes of the invention is that the use of a small amount of hydrogen, besides regulating the molecular weight, entails a considerable increase of the polymerization activities.

The catalysts according to the present invention can be used also in a process as described above for the copolymerization of propylene with one or more alpha-olefins such as for example ethylene, 1-butene, 1-pentene, 4-methyl-1-pentene, 1-hexene, 1-octene, 1-decene, 1-dodecene, 1-tetradecene, 1-esadecene, 1-octadecene, 1-eicosene, allylcyclohexene, cyclopentene, styrene, cyclohexene, norbornene and 4,6-dimethyl-1-heptene. Copolymers propylene/ethylene and propylene/1-butene are preferred. When 1-butene is used as comonomer, copolymers with relatively high molecular weight but relatively low melting point are obtained.

In the propylene/ethylene copolymers the addition of ethylene strongly reduces the molecular weight of the copolymers, that means that ethylene can be used as molecular weight regulating as well.

Another interesting use of the catalysts according to the present invention is in the copolymerization of ethylene with higher olefins. In particular, the catalysts of the invention can be used for the preparation of LLDPE.

Suitable olefins to be used as comonomers comprise a-olefins of the formula $CH_2=CHR^{20}$, wherein $R^{20}$ is an alkyl radical having from 1 to 10 carbon atoms or an aryl radical having from 6 to 20 carbon atoms, and cycloolefins. Examples of these olefins are propylene, 1-butene, 1-pentene, 4-methyl-1-pentene, 1-hexene, 1-octene, 1-decene, 1-dodecene, 1-tetradecene, 1-esadecene, 1-octadecene, 1-eicosene, allylcyclohexene, cyclopentene, styrene, cyclohexene, norbornene and 4,6-dimethyl-1-heptene.

The copolymers may also contain small proportions of units deriving from polyenes, in particular from straight or cyclic, conjugated or non conjugated dienes, such as 1,4-hexadiene, isoprene, 1,3-butadiene, 1,5-hexadiene and 1,6-heptadiene.

The units deriving from $\alpha$-olefins of formula $CH_2=CHR^2$, $R^{20}$ is an alkyl radical having from 1 to 10 carbon atoms or an aryl radical having from 6 to 20 carbon atoms, from cycloolefins and/or from polienes are present in the copolymers preferably in amounts ranging from 1% to 20% by mole.

The saturated elastomeric copolymers can contain ethylene units and $\alpha$-olefins and/or non conjugated diolefins able to cyclopolymerise. The unsaturated elastomeric copolymers can contain, together with the units deriving from the polymerisation of ethylene and $\alpha$-olefins, also small proportions of unsaturated units deriving from the copolymerization of one or more polyenes. The content of unsaturated units is preferably comprised between 0 and 5% by weight.

Non limitative examples of suitable $\alpha$-olefins comprise propylene, 1-butene and 4-methyl-1-pentene. Suitable non conjugated diolefins able to cyclopolymerise comprise 1,5-hexadiene, 1,6-heptadiene and 2-methyl-1,5-hexadiene.

Non limitative examples of suitable polyenes are:
(i) polyenes able to give unsaturated units, such as:
linear, non-conjugated dienes, such as 1,4-hexadiene trans, 1,4-hexadiene cis, 6-methyl-1,5-heptadiene, 3,7-dimethyl-1,6-octadiene and 11-methyl-1,10-dodecadiene;
bicyclic diolefins, such as 4,5,8,9-tetrahydroindene and 6 and 7-methyl-4,5,8,9-tetrahydroindene;
alkenyl or alkyliden norbornenes, such as 5-ethyliden-2-norbornene, 5-isopropyliden-2-norbornene and exo-5-isopropenyl-2-norbornene;
polycyclic diolefins, such as dicyclopentadiene, tricyclo-[$6.2.1.0^{2.7}$]4,9-undecadiene and the 4-methyl derivative thereof;
(ii) non-conjugated diolefins able to cyclopolymerise, such as 1.5-hexadiene, 1,6-heptadiene and 2-methyl-1, 5-hexadiene;
(iii) conjugated dienes, such as butadiene and isoprene.

A further interesting use of the catalyst of the present invention is for the preparation of 1-butene homopolymer.

A further interesting use of the catalysts according to the present invention is for the preparation of cycloolefin polymers. Monocyclic and polycyclic olefin monomers can be either homopolymerised or copolymerised, also with linear olefin monomers.

Polymerisation processes according to the present invention can be carried out in gaseous phase or in liquid phase, optionally in the presence of an inert hydrocarbon solvent either aromatic (such as toluene), or aliphatic (such as propane, hexane, heptane, isobutane and cyclohexane).

The polymerisation temperature generally ranges from about 0° C. to about 250° C. In particular, in the processes for the polymerization of propylene, it is generally comprised between 20° C. and 150° C., preferably between 40° C. and 90° C.

The polymerization pressure is ranging from 0,5 to 100 bar, preferably from 2 to 50 bar, and more preferably from 4 to 30 bar.

The molecular weight of the polymers can be also varied merely by varying the polymerization temperature, the type or the concentration of the catalytic components or by using molecular weight regulators such as, for example, hydrogen.

The molecular weight distribution can be varied by using mixtures of different metallocenes, or carrying out the polymerization in several steps at different polymerization temperatures and/or different concentrations of the molecular weight regulator.

The polymerization yields depend on the purity of the metallocene component of the catalyst. Therefore, in order to increase the yields of polymerization, metallocenes are generally used after a purification treatment.

The components of the catalyst can be brought into contact before the polymerization. The pre-contact concentrations are generally between 1 and $10^{-8}$ mol/l for the metallocene component (A), while they are generally between 10 and $10^{-8}$ mol/l for the component (B). The pre-contact is generally effected in the presence of a hydrocarbon solvent and, if appropriate, of small quantities of monomer. The pre-contact time is generally comprised between 1 minute and 24 hours.

FIG. 1 reports a computer generated diagram of the metallocene compound prepared in Example 1 based on X-ray crystallography data.

FIG. 2 reports a computer generated diagram of the metallocene compound prepared in Example 2 based on X-ray crystallography data.

The following examples are given to illustrate and not to limit the invention.

EXPERIMENTAL PART

General Materials and Procedures

All syntheses were performed under a nitrogen atmosphere in pre-dried glassware unless stated otherwise. Solvents for air-sensitive compounds were purified as follows:

THF, ether, and toluene were distilled from sodium/benzophenone, pentane was distilled from sodium/benzophenone/triglyme, dichloromethane was distilled from CaH$_2$ and stored over 4 A sieves. Methylalumoxane (10 wt % toluene sol.) was purchased from Witco Corp.

MS. Mass spectra of organic intermediates were measured with an HP 6890 series GC equipped with a 5973 mass selective detector.

Synthesis of Organo-aluminum Compounds for Examples 41–48

General Procedure

All reactions were carried out under nitrogen in the glove box or under Schlenk conditions using oven-dried glassware. The toluene solvent was dried over 4 Å molecular sieves. All alkenes were dried over 4 Å molecular sieves prior to use.

Tris(2-methyl-propyl)aluminum (TIBA) was obtained from Alrdrich and used as pure compound.

tris(2-Phenyl-propyl)aluminum—Al(CH$_2$CHMePh)$_3$ (TPPA)

In a glove box, alpha-methyl-styrene (283 g, 2.3 mol; Aldrich, dried over sieves) was dissolved in dry toluene (ca. 300 ml) in a 1 L 3-neck flask. Al{CH$_2$CHMe$_2$}$_3$ (TIBA, 100 ml, 0.395 mmol, ex-Witco) was added over 10 min by syringe to the rapidly stirred solution at ambient temperature. The reaction flask was removed from the glove box and a reflux condenser and nitrogen line attached in the fume hood. The isobutene product was collected using a graduated collection vessel immersed in a −78° C. acetone/dry ice bath. The reaction mixture was warmed over 90 minutes to an internal temperature of 110.7° C. The reaction was allowed to reflux for 16 hours (final reflux temperature 126.4° C.), affording ca. 100% of the theoretical maximum yield of isobutene (ca. 3.0 equivalents/Al). The remaining olefin and solvent were removed in vacuo (50° C., 0.05 mbar, 90 min) utilizing a dry ice/acetone bath to give 162 g of tris(2-phenyl-propyl)aluminum.

tris[2-(4-Fluoro-phenyl)propyl]aluminum—Al[CH$_2$CHMe(4-F—C$_6$H$_4$)]$_3$ (TFPPA)

In the glove box, 2-(4-fluoro-phenyl)-propylene (65.1 g, 0.48 mol; Acros, dried over sieves) was dissolved in dry toluene (ca. 70 ml) in a 250 ml 3-neck flask. Al{CH$_2$CHMe$_2$}$_3$ (TIBA, 27.9 ml, 0.120 mol, ex-Witco) was added over 10 min by syringe to the rapidly stirred solution. The reaction flask was removed from the glove box and a reflux condenser and nitrogen line attached in the fume hood. The isobutene product was collected using a graduated collection vessel immersed in a −78° C. acetone/dry ice bath. The reaction mixture was warmed over 90 minutes to an internal temperature of 119.6° C. The reaction was allowed to reflux for 16 hours (final reflux temperature 123.5° C.), affording ca. 100% of the theoretical maximum yield of isobutene. The remaining olefin and solvent were removed in vacuo (60° C., 0.05 mbar, 90 min) utilizing a dry ice/acetone bath to give 50 g of tris[2-(4-fluoro-phenyl)-propyl]aluminum.

tris(2,3 Dimethyl-butyl)aluminum) (TDMBA)

Tris(2,3 dimethyl-butyl)aluminum) was prepared according to WO 99/21899.

tris(2,4,4-Trimethyl-pentyl)aluminum (TIOA)

The aluminum compound was prepared according to the method described in Liebigs Ann. Chem., Volume 629, 1960, Ziegler et al. "Aluminiumtrialkyle und Dialkyl-aluminiumhydride aus Aluminiumisobutyl-Verbindungen [Aluminum trialrcyls and dialkyl-aluminum hydrides from aluminum isobutyl compounds]", pages 14–19.

PREPARATION OF THE METALLOCENES

EXAMPLE 1

Synthesis of Dimethylsilandiylbis-6-(2,5-dimethyl-3-phenylcyclotentadienyl-[1,2-b]-thiophene) zirconium Dichloride—{(2,5-Me$_2$-3-Ph-cyclopento[2,3-b]thiophen-6-yl)$_2$SiMe$_2$}ZrCl$_2$ (C3)

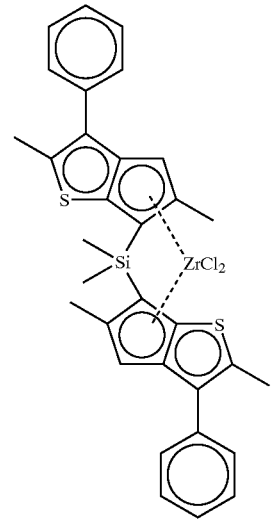

Synthesis of 3-Bromo-2-methylthiophene

To a solution containing 62.0 g (610 mmol, 88 mL) diisopropylamine dissolved in 150 mL THF was added a 2.5 M solution of butyllithium in hexane (610 mmol, 210 mL) while maintaining the temperature at 0° C. After addition was complete, stirring continued for an additional 30 minutes. The flask containing LDA was cooled to −78° C. then a solution containing 100 g (610 mmol) 3-bromothiophene dissolved in 60 mL THF was added dropwise. After addition was complete the solution was warmed to 0° C. (ice bath), then stirred an additional 30 min. The temperature of the reaction slurry was then lowered to −78° C., then a solution containing 86.5 g (610 mmol) iodomethane dissolved in 40 mL THF was added in one portion. The reaction mixture was stirred an additional 30 m at −78° C., then warmed to room temperature and stirred an additional 1 h. The organic layer was collected with diethylether, washed with water, dried over magnesium sulfate, filtered, then solvents were removed in vacuo. Light orange oil (89.8 g, 90.7% by GC) recovered. Yield: 74.8%. $^1$H-NMR δ (CDCl$_3$): 7.1 (d, 1H), 6.9 (d, 1H) 2.4 (s, 3H). $^{13}$C-NMR (CD$_2$Cl$_2$): δ 134.6, 130.3, 123.3, 109.8, 14.8. EIMS: m/z (%) 176,178 (M$^+$, 57), 97 (100), 81 (4), 69 (12) 53 (14).

Synthesis of 2-Me-3-Phenylthiophene

To a slurry containing 3-Bromo-2-methylthiophene (89.8 g, 460 mmol) and 1 g of [bis(diphenylphosphino)propane)] dichloronickel (Ni(dppp)Cl$_2$ in 200 mL diethylether was added a solution containing phenylmagnesium bromide in diethyl ether (456 mmol, 3 M, 152 mL), dropwise. After addition was complete, the reaction flask was stirred an additional 1 h, then quenched with water. The organic fraction was extracted with dichloromethane, washed with water, dried over magnesium sulfate, then the solvents removed in vacuo. A dark orange oil. (77.13 g, 87.2% by GC) was recovered. Yield: 84.7%. $^1$H-NMR (δ, PPM, CDHCl$_2$): 7.3–7.6 (m, 5H), 7.1–7.25 (m, 2H), 2.6 (s, 3H). $^{13}$C-NMR (CD$_2$Cl$_2$): δ 139.1, 137.2, 134.6, 129.6, 129.2, 129.1, 128.9, 128.8, 127.7, 127.5, 127.1, 122.0, 14.4. EIMS: m/z (%) 176 (6), 175 (18), 174 (100), 173 (98), 172 (6), 171 (14), 158 (2), 147 (9), 141 (15), 135 (4), 129 (18) 115 (15).

Synthesis of 2,5-Me$_2$-3-Ph-5,6-Dihydrocyclopenta[1,2-b]thiolphen-4-one

A solution containing 2-Me-3-Phenylthiophene (124.7 g, 542 mmol), methacrylic acid (61.7 g, 715 mmol), and 200 mL dichloromethane was added slowly to 1000 g of super PPA stirring at 70° C. The flask and contents were refluxed for 10 h, with an additional 208 g of methacrylic acid in 250 mL dichloromethane added in 60 or 75 g portions during the reaction. After stirring for 10 h, the reaction mixture was poured onto ice. The organic layer was collected with 20% (v/v) dichloromethane in hexane, washed with water, a saturated solution of sodium hydrogen carbonate, and then water. The organic layer was dried over magnesium sulfate, filtered, then solvents were removed in vacuo leaving a dark brown oil. Yield: 202.9 g (81.7% by GC, 95.6%): used in subsequent steps without additional purification. Note: Two isomers of 16 were recovered in a ratio of 3:1. $^1$H-NMR (CD$_2$Cl$_2$): δ 7.05–7.4 (m, 5H), 2.6–3.0 (m, 2H), 2.3 (s, 3H), 1.7–1.85 (m, 1H), 1.1 (d, 3H). $^{13}$C-NMR (CD$_2$Cl$_2$): δ 199.9, 167.6, 152.1, 136.5, 134.6, 130.4, 129.6, 139.4–127.1, 46.5, 33.8, 17.1, 17.0, 16.2. EIMS: m/z (%) 242 (100), 227 (54), 214 (10), 213 (17), 199 (38), 185 (21), 184(11), 165 (14), 152 (8), 139 (4), 128 (5), 115 (12).

Synthesis of 2,5-Me$_2$-3-Ph-4,5,6-Trihydrocyclopenta[1,2-b]thiophen-4-ol

A 1.0 M solution of lithium aluminum hydride in ether (300 mmol, 300 mL) was added dropwise at 0° C. to 202 g of 2,5-Me$_2$-3-Ph-5,6-dihydrocyclopenta[1,2-b]thiophen-4-one dissolved in of THF. After addition was complete, the temperature of the reaction flask was raised to room temperature, then stirred an additional 2 h. The reaction was quenched with water, the organic layer was collected with ether, washed with water, dried over magnesium sulfate, filtered, and then the solvents were removed in vacuo. Multiple isomers of the product were recovered. An additional 16 g of material was recovered by repeated washing of the lithium-prill. The product was recovered as a yellow solid Yield: 139.1 (75%), 78.5% by GC: used in subsequent steps without additional purification. $^1$H-NMR (CD$_2$Cl$_2$): δ 7.2–7.8 (m, 4H), 4.9 (0.5H), 4.8 (0.5H), 2.6–3.2 (m, 3H), 2.4–2.6 (m, 3H), 1.1–1.3 (m, 3H). $^{13}$C-NMR (CD$_2$Cl$_2$): δ 146.8, 140.2, 136.4, 129.5, 129–127, 80.8, 74.4, 73.7, 49.0, 43.9, 35.7, 35.4, 35.2, 19.4, 15.3, 15.27, 14.7. EIMS: m/z (%) 244 (100), 229 (48), 211 (26), 201 (21), 188 (10) 187 (12), 185 (15), 184 (14), 165 (16), 153 (11), 152 (13), 115 (17).

Synthesis 2,5-Me$_2$-3-Ph-6-Hydrocyclotpenta[1,2-b]thiophene

To a solution containing 28 g (114.3 mmol) of 2,5-Me$_2$-3-Ph-4,5,6-Trihydrocyclopenta[1,2-b]thiophen-4-ol dissolved in 100 mL of toluene was added a 1 g portion of p-toluene sulfonic acid (p-TSA) and the mixture was refluxed for 30 min. The reaction mixture was quenched with water and the organic layer was separated. The organic layer was washed with bicarbonate, water, dried (MgSO$_4$), then the solvents were removed in vacuo. Dark red oil was recovered (two isomers). Yield: 26.6 g (90%), 87% by GC. $^1$H-NMR (CD$_2$Cl$_2$): 6.8–7.6 (m, 5H), 6.1–6.3 (2s, 1H), 3.1, 2.9 (s, 2H), 2.3 (m, 3H), 1.9 (m, 3H). $^{13}$C-NMR (CD$_2$Cl$_2$): δ 150.6, 146.9, 145.9, 145.6, 141.0, 137.0, 136.8, 135.8, 134.3, 131.3, 129.5, 129.1, 128.8, 127.1, 126.9, 123.5, 122.4, 41.0, 40.8, 17.2, 17.1, 15.1, 15.0. EIMS: m/z (%) 227 (20), 226 (100), 225 (34), 211 (34), 210 (17), 209 (10), 193 (19), 178 (28).

Synthesis of (2,5-Me$_2$-3-Ph-6-Hydrocyclopenta[2,3-b]thiophen-6-yl)$_2$SiMe$_2$ To a solution containing 22.6 g (100 mmol) of 2,5-Me$_2$-3-Ph-6-hydrocyclopenta[1,2-b]thiophene dissolved in THF (80 mL) was added a 2.5 M solution of n-butyllithium in hexane (100 mmol, 40 mL) at room temperature. The contents of the flask were stirred for an additional 5 h. In a separate flask was added 6.45 g (50 mmol) of dichlorodimethylsilane dissolved in THF (40 mL). The temperature was lowered to –78° C., then the THF solution containing anion prepared above was added dropwise. After addition was complete, the flask and contents were allowed to warm to room temperature and stirred for 6 h. The reaction mixture was poured onto water, then the organic fraction was collected with dichloromethane, dried over magnesium sulfate, and concentrated in vacuo. The solids were recrystallized from ether, collected on a medium glass frit filter, and dried in vacuo producing an off white powder: Yield: 11.33 g (45%), 99% by GC. $^1$H-NMR (CD$_2$Cl$_2$): δ 7.2–7.6 (m, 10H), 6.2, 6.5, 6.55 (s, 2H), 3.85, 4.08 (s, 2H), 2.5 (s, 6H), 2.1–2.4 (m, 6H), –0.2, –0.55, –0.75 (s, 6H). $^{13}$C-NMR (CD$_2$Cl$_2$): δ 136.9, 135.7, 129.5–122.44, 123.4–121.7, 68.2, 40.8, 40.7, 18.1, 17.7, 15.0, –202, –2.5. EIMS: m/z (%) 509.1 (9) 508 (22) 283 (100), 255 (10), 241 (6), 210 (6), 178 (18), 152 (3).

Synthesis of {(2,5-Me$_2$-3-Ph-Cyclopento[2,3-b]thiophen-6-yl)$_2$SiMe$_2$}ZrCl$_2$ To a solution containing 1.82 g (3.6 mmol) of (2,5-Me$_2$-3-Ph-6-hydrocyclopenta[2,3-b]thiophen-6-yl)$_2$SiMe$_2$ slurried in 100 mL of diethylether was added a 2.5 M solution of n-butyllithium in hexane (2.9 mL, 7.2 mmol) dropwise at room temperature. Stirring was continued for 5 h., then 0.83 g (3.6 mmol) of zirconium tetrachloride was added slowly as a dry powder. The reaction mix was stirred an additional 3 h, then the solution was filtered. The solids collected in this fashion were washed with ether, then the solvents were removed in vacuo leaving 770 mg of a 3:5 rac/meso mixture. The solids remaining on the filter were then slurried in dichloromethane, filtered, and the solvents were removed from the solution in vacuo. 350 mg pure-rac isomer was recovered. Yield: 1.12 g (47%). $^1$H-NMR (CD$_2$Cl$_2$): δ 7.25–7.6 (m, 10H, rac), 6.58 (s, 2H, rac), 2.55 (s, 3H, rac), 2.3 (s, 3H, rac), 1.05 (s, 6H, rac). $^{13}$C-NMR (CD$_2$Cl$_2$): δ 168.8, 147.6, 145.3, 135.5, 135.4, 129.95, 129.47, 128.2, 119.0, 85, 19.9, 16.0, 0.0. EIMS: m/z 669 (M$^+$+1 of theo).

EXAMPLE 2

Synthesis of Dimethylsilandiylbis-6-[2,5-dimethyl-3-(2'-methyl-phenyl)cyclotentadienyl-[1,2-b]-thiophene]zirconium Dichloride—{(2,5-Me$_2$-3-(2MePh)-Cyclopento[2,3-b]thiophen-6-yl)$_2$SiMe$_2$}ZrCl$_2$ (C4)

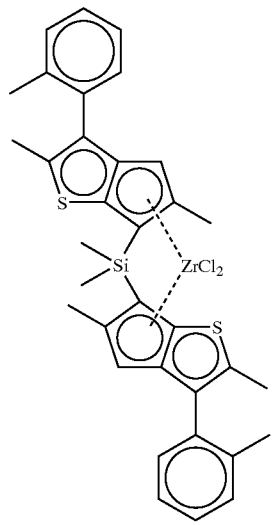

Synthesis of 2-Me-3-(2-MePh)-Thiophene

An ether solution of o-tolylmagnesium bromide (350 mL, 2.0 M, 0.7 mol) was added slowly to a mixture of 3-bromo-2-methylthiophene previously prepared (123 g, 0.7 mol) and 1.2 g of Ni(dppp)Cl$_2$ in 50 mL of ether. After stirring overnight, water (200 mL) was added slowly to the reaction mixture at room temperature. The organic layer was separated, washed with brine solution (100 mL), and dried (MgSO$_4$). Solvents were removed in vacuo. Yield: 136 g: used without further purification. $^1$H-NMR (CDCl$_3$): δ 7.2–7.4 (m, 4H), 7.18 (t, 1H), 6.98 (t, 1H), 2.35 (d, 3H), 2.27 (d, 3H). EIMS: m/z (%) 188 ([M$^+$], 100), 173 (62), 155 (34), 141 (9), 128 (33), 115 (15).

Synthesis of 2,5-Me$_2$-3-(2-MePh)-5,6-Dihydrocyclopenta[1,2-b]thionhen-4-one A solution of 2-Me-3-(2-MePh)-thiophene (80 g, 0.43mol) and methacrylic acid (44 g, 0.51 mol) in 100 mL of dichloroethane was added dropwise to 1000 g of super PPA at 80° C. and stirred for 5 h. The dark red mixture was poured onto crushed ice (1000 g) and stirred until the PPA was completely decomposed. The product was extracted with 30% (v/v) dichloromethane in hexane (2×400 mL). The combined organic fractions were washed with a saturated aqueous solution of NaHCO$_3$ and dried (MgSO$_4$). Solvents were removed on a rotoevaporator leaving 74 g of product used without further purification. $^1$H-NMR (CDCl$_3$): δ 7.1–7.3 (m, 3H), 7.0 (d, 1H) 2.7–3.0 (m, 2H), 2.25 (s, 3H), 2.18 (m, 1H), 2.05 (s, 3H), 1.2 (d, 3H). $^{13}$C-NMR (CDCl$_3$): δ 199.6, 167.3, 152.2, 136.6, 135.9, 133.4, 130.2, 129.7, 128.1, 125.8, 46.1, 46.0, 32.8, 19.5, 16.9, 15.4. EIMS: m/z (%) 256 ([M$^+$], 85), 241 (100), 227 (6), 213 (35), 199 (22), 184 (7), 165 (15), 152 (9), 128 (11).

Synthesis of 2,5-Me$_2$-3-(2-MePh)-6-Hydrocyclopenta[1,2-b]thiophene

A solution of 2,5-Me$_2$-3-(2-MePh)-5,6-dihydrocyclopenta[1,2-b]thiophen-4-one (74 g, 0.286 mol) in 200 mL of THF was treated with 145 mL of LiAlH$_4$ in THF (1.0 M, 0.145 mol) at 0° C. After stirring at room temperature for 3 h, water was added cautiously (50 mL) and the resulting slurry was filtered. THF was evaporated from the filtrate and the solid filter cake was washed with dichloromethane (3×150 mL). The dichloromethane wash and filtrate residue were combined, washed with water (50 mL), dried (MgSO$_4$), and evaporated to a brown liquid (67.2 g). The crude product was re-dissolved in 250 mL of toluene and stirred with 2.0 g of p-TSA at 70° C. for 1.5 h. After cooling, the toluene solution was washed with water (50 mL), NaHCO$_3$ solution (50 mL), brine solution (50 mL), and dried (MgSO$_4$). Solvents were removed on a rotoevaporator leaving brown oil. Distillation (120° C., 0.05 torr) gave a light yellow liquid. Yield: 47 g (68%). Two isomers—$^1$H-NMR (CDCl$_3$): δ 7.1–7.3 (m, 4H), 6.7 (m, 1H), 6.4 (m, 1H), 3.6 (s, 2H), 3.2 (ss, 2H), 2.6 (s, 3H), 2.55 (s, 3H), 2.47 (s, 3H), 2.46 (s, 3H), 2.42 (s, 3H), 2.40 (s, 3H). $^{13}$C-NMR (CDCl$_3$): δ 146.2, 145.2, 137.0, 136.4, 134.2, 133.7. 130.2, 130.0, 129.5, 127.5, 127.4, 125.7, 123.4, 122.4, 40.1, 19.9, 17.1, 14.4. EIMS: m/z (%) 240 ([M$^+$], 100), 225 (65), 210 (10), 192 (20), 178 (8), 165 (15), 149 (5), 128 (5). Analytical data for the lithium salt of 2,5-Me$_2$-3-(2-MePh)-6-hydrocyclopenta[1,2-b]thiophene prepared by reaction with n-bultylithium—$^1$H-NMR (THF-d$_8$): δ 7.2 (m, 2H), 7.1 (m, 2H), 5.5 (d, 1H), 5.22 (d, 1H), 2.19 (s, 3H), 2.15 (s, 3H). $^{13}$C-NMR (THF-d$_8$): δ 140.3, 137.9, 131.2, 130.5, 126.8, 125.7, 124.1, 120.1, 117.2, 92.4, 91.9, 20.6, 16.4, 15.2.

Synthesis of (2,5-Me$_2$-3-(2MePh)-6-Hydrocyclopenta[2,3-b]thiophen-6-yl)$_2$SiMe$_2$ A solution of 2,5-Me$_2$-3-(2-MePh)-6-hydrocyclopenta[1,2-b]thiophene (36.9 g, 0.154 mol) in mL of THF was cooled to −78° C. and treated with 62 mL of n-butyllithium in hexanes (2.5 M, 0.155 mol). After stirring for 16 h at room temperature, the solution was added dropwise to a solution of dichlorodimethylsilane (9.94 g, 0.077 mol) in 70 mL of THF stirring at −78° C. The reaction mixture was slowly warmed to room temperature and stirred for 2 days. A saturated aqueous solution of NH$_4$Cl was added slowly (10 mL) and most of the THF was removed on a rotoevaporator. The residue was partitioned with ether (500 mL) and water (150 mL). The water layer was separated, re-extracted with fresh ether (100 mL), and the combined ether fractions were dried (MgSO$_4$). Evaporation of solvent yielded 41 g of product as an off-white solid (91% purity by GC). 18.7 g of crude product were chromatographed on silica (5% CH$_2$Cl$_2$/hexane) giving 13.3 g of the target as a mixture of isomers. EIMS: m/z (%) 536 ([M$^+$], 22), 297 (100), 281 (6), 223 (5), 192 (12), 165 (6). The proton NMR spectrum showed a complex mixture of isomers. Analytical data for the lithium salt of (2,5-Me$_2$-3-(2MePh)-6-hydrocyclopenta[2,3-b]thiophen-6-yl)$_2$SiMe$_2$ prepared by reaction with n-bultylithium—$^1$H-NMR (THF-d$_8$): δ 7.08–7.18 (m, 8H), 5.43 (s, 2H), 2.28 (d, 3H), 2.21 (d, 3H), 1.19 (s, 3H), 0.89 (d, 3H), 0.63 (s, 3H).

Synthesis of {(2,5-Me$_2$-3-(2MePh)-Cyclopento[2,3-b]thiophen-6-yl)$_2$SiMe$_2$}ZrCl$_2$ A solution of (2,5-Me$_2$-3-(2-MePh)-6-hydrocyclopenta[2,3-b]thiophen-6-yl)$_2$SiMe$_2$ (27.6 g, 51.5 mmol) in 200 mL of ether was cooled to −78° C. and treated with 42 mL of n-butyllithium in hexanes (2.5 M, 105 mmol). After stirring overnight at room temperature, solvents were removed in vacuo and pentane (150 mL) was added. The yellow slurry was cooled to −78° C. and treated with ZrCl$_4$ (11.7 g, 50.2 mmol). The reaction mixture was warmed to room temperature, stirred for 18 h, and filtered through a closed frit. The yellow solids were washed with pentane (60 mL) and dried under vacuum giving 33.8 g of crude product. The crude product was stirred in 400 mL of dichloromethane at room temperature and filtered through celite. Evaporation of the filtrate under reduced pressure gave the product as a 50/50 rac/meso mixture (27.9 g, 78.5%). The isomers were separated by dissolving a portion of the rac/meso mixture in dichloromethane, adding an equal volume of hexane, and partial evaporation of dichloromethane under reduced pressure. In this way the meso isomer was precipitated from the solution and removed by filtration. After a second filtration, solvents were removed from the filtrate giving the rac isomer in ca. 95% purity. $^1$H-NMR (CD$_2$Cl$_2$): δ 7.65 (m, 2H, meso), 7.60 (m, 2H, rac), 7.27 (m, 6H, meso), 7.26 (m, 6H, rac), 6.33 (s, 2H, rac), 6.18 (s, 2H, meso), 2.34 (s, 6H, rac), 2.32 (s, 6H, meso), 2.30 (s, 6H, rac) 2.25 (s, 6H, meso), 2.09 (s, 6H, rac), 2.03 (s, 6H, meso), 1.17 (s, 3H, meso), 1.13 (s, 3H, meso), 1.08 (s, 6H, rac). $^{13}$C-NMR (CD$_2$Cl$_2$): δ (rac isomer) 148.1, 145.6, 137.3, 134.6, 134.4, 130.8, 130.4, 129.6, 128.2, 126.3, 125.2, 118.5, 19.5, 19.47, 15.2, −0.57. EIMS: m/z 697 (M$^+$+1 of theo).

EXAMPLE 3
Synthesis of Dimethylsilandiylbis-6-[3,5-dimethylcyclolentadienyl-[1,2-b]-thiophene]zirconium Dichloride—SiMe$_2$(Me$_2$CpThionhen)ZrCl$_2$ (C6)

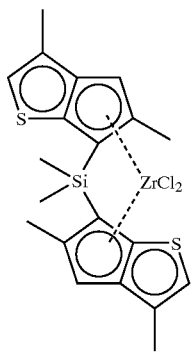

Synthesis of 3,5-Dimethyl-6-Hydrocyclopenta[1,2-b] thiophen-4-one

To a flask containing 950 g of 84% polyphoshopric acid (Aldrich) was added 180 g of P$_2$O$_5$. The slurry was heated to 140° C. for 4 h (until al P$_2$O$_5$ had dissolved), then cooled to 70° C. Dropwise, a solution containing 100 g (1.01 mol) 3-methylthiophene, 86 g (1 mol) methacrylic acid, and 60 ml dichioromethane was added. The mixture was refluxed for 2 h then the solution was poured onto ice. The organic layer was collected with a 30% dichloromethane/hexane solution which was washed with water, saturated bicarbonate solution, water, then dried over magnesium sulfate, filtered, then the solvents were removed in vacuo. 143 g of dark brown oil was recovered. The oil was distilled at 78° C. at 500 microns; 10.2 g of pale yellow oil was recovered (yield, 6.1%). The title compound was analysed by means of $^1$H-NMR spectroscopy.

Synthesis of 3,5-Dimethyl-4-sulfonohydrazide-6-hydrocyclopenta[1,2-b]thiophene

To a flask containing 9.5 g (57 mmol) 3,5-dimethyl-6-dihydrocyclopenta[1,2-b]thiophen-4-one dissolved in 100 ml ethanol was added 10.6 g (57 mmol) para-toluenesulfonohydrazide and a catalytic amount (0.6 g) para-toluenesulfonic acid monohydrate. The reaction mixture was refluxed for 2 h, then cooled to room temperature. The cooled solution was filtered and the white precipitate collected by filtration. The solids were dried in vacuo; 12.8 g (yield: 67.4%) of material were collected in this fashion. The title compound was analysed by means of $^1$H-NMR spectroscopy.

Synthesis of 3,5-Dimethyl-6-hydrocyclopenta[1,2-b] thiophene

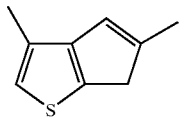

To a flask containing 11.1 g (33.3 mmol) 2-sulfonohydrazide-3,5-dimethyl-4-hydrocyclopenta[1,2-b] thiophene dissolved in 50 ml THF was added a solution containing 2.5 M n-butyllithium (96 mmol, 38.4 ml) in hexane. Stirring was continued for 18 h then the reaction was quenched with a solution containing 18 g (1 mol) water dissolved in 48 ml THF added at 0° C. An additional 100 ml water was added, then the THF was removed in vacuo. The organic fraction was collected with a 20% dichloromethane in hexane solution which was washed with water, saturated sodium bicarbonate solution, then water, dried over magnesium sulfate, then filtered. Solvents were removed on a rotoevaporator yielding 2.9 g of dark orange oil, which was used in subsequent steps without further purification. The title compound was analysed by means of $^1$H-NMR spectroscopy.

Synthesis of bis(3,5-Dimethylthiopentalene)dimethylsilane

To 2.9 g (20 mmol) of 3,4-dimethyl-6-hydrocyclopenta [1,2-b]thiophene dissolved in 20 ml diethylether was added a 2.5 M solution containing n-butyllithium (20 mmol, 8ml) in hexane. Stirring continued for 2 h., then the solvents were removed in vacuo. The dried solids were washed with pentane, then dissolved in 10 ml THF. In a separate flask, a solution containing 1.2 g (10 mmol) dichlorodimethylsilane and the THF solution containing the anion was added dropwise. Stirring continued for 18 h., then the solvents were removed in vacuo. The solids were washed with pentane, then pentane was removed in vacuo yielding 3.0 g of a tan free flowing powder. The title compound was analysed by means of $^1$H-NMR spectroscopy.

Synthesis of Dimethylsilandiylbis(3,5dimethylthiopentalene)zirconium Dichloride

A 250 ml flask was charged with 3.0 g (8.41 mmol) bis(3,5-dimethylcyclopenta[1,2-b]thiophene)dimethylsilane dissolved in 60 ml diethylether. Dropwise at room temperature, a solution containing 2.5 M butyllithium in hexane (16.8 mmol, 7 ml) was added. The solution was stirred for 1.5 h. then the solvents were removed in vacuo. The solids were washed with pentane, and the dianion was obtained as a light brown powder. The title compound was analysed by means of $^1$H-NMR spectroscopy.

The dianion (prepared above) was slurried in pentane (70 ml) then zirconium tetrachloride 1.96 g, 8.41 mmol) was slowly added as a dry powder. After addition was complete, a few drops of THF was added, then the slurry was stirred 18 h. Solvents were removed in vacuo, then 4.5 g of a bright yellow solid were recovered. A 3.5 g portion of this material was purified by filtering from dichloromethane and the solvents again removed in vacuo yielding 1.3 g of a 50/50 rac meso mixture; calculated yield 1.68 g (38.8%). Crystals of the rac isomer were obtained by slow evaporation of a dichloromethane solution of the rac/meso mixture. The title compound was analysed by means of $^1$H-NMR spectroscopy.

EXAMPLE 4

Synthesis of Dimethylsilandiylbis-6-[2,5-dimethyl-3-(2',5'-dimethyl-phenyl)cyclopentadienyl-[1,2-b]-thiophene]zirconium Dichloride (C5)

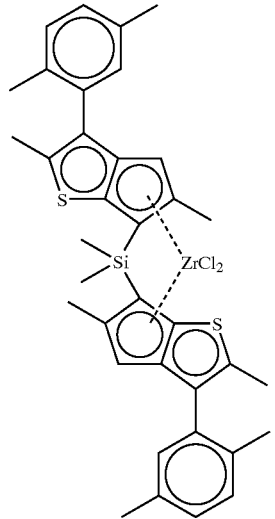

Synthesis of 2-Me-3(2,5-Me$_2$Ph)Thiophene

An ether solution of 2,5-dimethylphenylmagnesium bromide (400 mL of a 0.6 M, 0.24 mol) was added slowly to a mixture of 3-bromo-2-methylthiophene (42.5 g, 0.24 mol) and 1.2 g of Ni(dppp)Cl$_2$ in 100 mL of ether. After stirring overnight, water (200 mL) was added cautiously and the organic layer was separated, washed with brine solution (100 mL), and dried (MgSO$_4$). Evaporation of solvent and starting material yielded 47 g of product used without further purification. EIMS: m/z (%) 202 (M$^+$, 100), 187 (78), 171 (29), 154 (15), 128 (16), 115 (13).

Synthesis of 2,5-Me$_2$-3-(2,5-Me$_2$Ph)-5,6-Dihydrocyclopenta[1,2-b]thiolphen-4-one A solution of 2-Me-3-(2,5-Me$_2$Ph)thiophene (47 g, 0.23 mol) and methactylic acid (24 g, 0.28 mol) in 125 mL of dichloroethane was added dropwise to 1000 g of super PPA at 90° C. and stirred for 24 h. The dark red mixture was poured onto crushed ice (1000 g) and stirred until the PPA was completely decomposed. The product was extracted with 25% (v/v) dichloromethane in hexane (2×400 mL). The combined organic fractions were washed with a saturated aqueous solution of NaHCO$_3$ and dried (MgSO$_4$). Solvents were removed on a rotoevaporator leaving 59 g of brown oil. The product was purified by chromatography on silica with 50% (v/v) dichloromethane in hexane. Yield: 26.1 g (42%). $^1$H-NMR (CDCl$_3$): δ 7. (d, 1H), 7.15 (d, 1H), 6.92 (s, 1H), 2.95 (m, 2H), 2.5 (m, 1H), 2.38 (s, 1H), 2.35 (s, 3H), 2.1 (s, 3H), 1.32 (s, 3H). $^{13}$C-NMR (CDCl$_3$): δ 152.1, 136.2, 135.9, 135,3, 133.5, 133.3, 130.22, 130.20, 130.11, 128.9, 122.5, 46.1, 32.9, 20.8, 19.1, 16.9, 15.4. EIMS: m/z (%) 270 (M$^+$, 86), 255 (100), 241 (6), 227 (37), 213 (25), 198 (11), 179 (10), 141 (7), 128 (15).

Synthesis of 2,5-Me$_2$-3-(2,5-Me$_2$Ph)-6-Hydrocyclopenta[1,2-b]thiophene

A solution of 2,5-Me$_2$-3-(2,5-Me$_2$Ph)-5,6-dihydrocyclopenta[1,2-b]thiophen-4-one (26.1 g, 97 mmol) in 75 mL of THF was treated with 48 mL of LiAlH$_4$ in ether (1.0 M sol., 48 mmol) at 0° C. After stirring at room temperature for 5 h, water was added cautiously (10 mL) and the resulting slurry filtered through a plug of celite. THF was evaporated from the filtrate and the filter cake was washed with dichloromethane (3×50 mL). The dichloromethane fractions were combined with the filtrate residue and washed with water (50 mL). After drying (MgSO$_4$), the solvent was removed on a rotoevaporator. The product was dissolved in toluene (60 mL) and stirred with 0.4 g of p-TSA at 60° C. for 3 h. After cooling, the toluene solution was washed with water (50 mL), NaHCO$_3$ solution (50 mL), brine solution (50 mL), and dried (MgSO$_4$). Toluene was removed on a rotoevaporator and the product was purified by distillation (110° C., 0.05 torr). Yield: 11.5 g (47%). $^1$H-NMR (CDCl$_3$): δ 7.19 (d, 1H), 7.1 (d, 1H), 7.0 (s, 1H), 6.41(s, 1H), 2.93 & 2.90 (ss, 2H, 2 isomers), 2.35 (s, 3H), 2.25 (s, 3H), 2.12 (s, 6H). $^{13}$C-NMR (CDCl$_3$): δ 146.0, 149.9, 140.1, 136.0, 134.8, 134.1. 133.6, 133.3, 130.4, 129.8, 128.0, 122.1, 39.9, 20.9, 19.1, 16.9, 14.2. EIMS: m/z (%) 254 (M$^+$, 100), 239 (75), 224 (16), 206 (20), 191 (11), 16.9, 149 (6), 128 (9).

Synthesis of (2,5-Me$_2$-3-(2,5-Me$_2$Ph)-6-Hydrocyclopenta[2,3-b]thiophen-6-yl)$_2$SiMe$_2$ A solution of 2,5-Me$_2$-3-(2,5-Me$_2$Ph)-6-hydrocyclopenta[1,2-b]thiophene (10.6 g, 41.7 mmol) in 60 mL of THF was cooled to −78° C. and treated with 17 mL of n-butyllithium in hexanes (2.5 M sol., 42.5 mmol). After stirring for 16 h at room temperature, the reaction mixture was added dropwise to a solution of dichlorodimethylsilane (2.69 g, 20.9 mmol) in 30 mL of THF at −78° C. The cold bath was removed and stirring continued for 18 h at room temperature before quenching with a saturated aqueous solution of Nh$_4$Cl (10 mL). The reaction product was diluted with ether (250 mL) and washed with water (100 mL). After drying (MgSO$_4$), solvents were removed on a rotoevaporator. The product was purified by chromatography on silica with 5% (v/v) dichloromethane in hexane. Yield: 7.0 g (59%) Major isomer—$^1$H-NMR (CDCl$_3$): δ 6.9–7.2 (m, 6H), 6.2 (s, 2H), 3.85 (s, 2H), 2.35(s, 6H), 2.25 (s, 6H), 2.20 (s, 6H), 2.10 (s, 6H), −0.12 (m, 6H). $^{13}$C-NMR (CDCl$_3$): δ 149.7, 146.2, 145.9 135.8, 135.6, 134.9, 134.8, 130.8 129.9, 127.8, 123.0, 122.1, 46.2, 20.9, 19.4, 18.0, 14.3, −7.5, −8.9. EIMS: m/z (%) 564 (M$^+$, 25), 311 (100), 282 (6), 253 (4), 237 (5), 206 (12), 189 (5), 165 (3), 128 (3).

Synthesis of {Me$_2$Si(2,5-Me$_2$-3-(2,5-Me$_2$Ph)Cyclopento[2,3-b]thiophen-6-yl)$_2$}ZrCl$_2$ A solution of (2,5-Me$_2$-3-(2,5-Me$_2$Ph)-6-hydrocyclopenta[2,3-b]thiophen-6-yl)$_2$SiMe$_2$ (2.33 g, 4.1 mmol) in 50 mL of ether was treated with 3.4 mL of n-butyllithium in hexanes (2.5 M sol., 8.5 mmol). After stirring overnight at room temperature, solvents were removed in vacuo and ZrCl$_4$ (0.96 g, 4.1 mmol) was added. Pentane (60 mL) was added and the mixture was stirred for 24 h. The solids were collected on a closed flit, washed with pentane, and dried under vacuum. The crude product was stirrer in 100 mL of dichloromethane and filtered through celite. The solvent was removed under reduced pressure giving the product as yellow solids (2.5 g, 50/50 rac/meso mixture). A portion of the product was re-dissolved in dichloromethane and treated with heptane giving a light yellow precipitate that was removed by filtration. The filtrate was concentrated under reduced pressure until the solution became cloudy. Upon standing, the rac isomer crystallized from the solution and was collected on a closed frit. $^1$H-NMR (CD$_2$Cl$_2$): δ 7.43 (s, 2H, meso), 7.40 (s, 2H, rac), 7.16 (d, 2H, rac), 7.15 (d, 2H, meso), 7.10 (d, 2H, rac), 7.09 (d, 2H, meso), 6.32 (s, 2H, rac), 6.19 (s, 2H, meso), 2.34 (ss, 12H, meso), 2.33 (ss, 12H, rac), 2.29 (s, 6H, rac), 2.25 (s, 6H, meso), 2.02 (s, 6H, rac), 1.19 (s, 3H, meso), 1.15 (s, 3H, meso), 1.10 (s, 6H, rac). $^{13}$C-NMR (CD$_2$Cl$_2$): δ (rac isomer) 148.0, 145.5, 135.7, 134.5, 134.2, 134.1, 131.3, 130.3, 129.9, 128.9, 125.2, 118.5, 21.1, 19.5, 19.3, 15.2, −0.58. EIMS: m/z 725 (M$^+$+1 of theo).

EXAMPLE 5

Synthesis of 5-Me-5,6-Dihydrocyclopenta[1,2-b]selenophen-4-one.

A solution of selenophene (9.9 g, 75.6 mmol) and methacrylic acid (7.8 g, 90 mmol) in 50 mL of dichloroethane was added dropwise to 250 g of super polyphosphoric acid (super PPA) at 80° C. and stirred for 1.5 h. The mixture was poured onto crushed ice and stirred until the PPA was completely decomposed. The product was extracted with 30% (v/v) dichloromethane in hexane. The combined organic fractions were washed with a saturated aqueous solution of NaHCO$_3$ and dried (MgSO$_4$). Solvents were removed on a rotoevaporator leaving 5.25 g of crude product that was 35% product by GC analysis. The crude product was chromatographed on silica (dichloromethane solvent) gave 3.02 g of the target. Yield: 35%. $^1$H-NMR (CD$_2$Cl$_2$): 8.6 (d, 1H), 7.25 (d, 1H), 3.25 (dd, 1H), 2.9 (m, 1H), 2.58 (dd, 1H), 1.3 (d, 3H); $^{13}$C 201.8, 169.5, 145.5, 144.7, 143.3, 126.3, 45.9, 34.4, 16.8; EIMS: m/z (%); 200 (88), 185 (100), 171 (13), 157 (22), 145 (7), 130 (9), 120 (11) 91 (55).

Synthesis of 5-Me-5,6-Dihydrocyclopenta[1,2-b]selenophen-4-ol

In a 250 mL flask was placed 20 g (100 mmol) 5-Me-5,6-dihydrocyclopenta[1,2-b]selenophen-4-one dissolved in 60 mL diethyl ether. Dropwise, a solution containing lithium aluminum hydride (1.0 M in diethylether, 100 mmol, 100 mL) was added at −78° C. After addition was complete, the temperature was allowed to warm to ambient, then stirred an additional 3 h. Water was then slowly added (50 mL) and the organics were filtered through Celite, collected with diethyl ether, washed with water, then dried (magnesium sulfate). The solvents were removed in vacuo: 12.86 g dark red oil: two isomers: 98.6% by GCMS; EIMS: m/z (%, major isomer); 205 (2), 204 (19), 203 (14), 202 (100), 201 (21), 200 (51), 199 (26), 198 (22), 187 (51), 186 (40), 184 (29), 183 (41), 182 (17), 181 (19), 180 (10), 175 (5), 174 (9), 173 (24), 172 (6), 171 (16), 170 (9), 169 (15);

Synthesis of 5-Me-3-Hydrocyclopenta[1,2-b]selenophene

In a 500 mL flask was placed 13 g (65 mmol) 5-Me-5,6-dihydrocyclopenta[1,2-b]selenophen-4-ol dissolved in 70 mL toluene and 0.2 g para-toluene sulfonic acid monohydrate. The flask contents were stirred at room temperature for 18 h., then the reaction mixture was washed with water, the organics were collected with diethyl ether, dried over magnesium sulfate, filtered, then solvents were removed in vacuo. 12.3 g of dark red oil was collected. 11 g were chromatographed with hexane through silica: 0.6 g of a light yellow oil were collected from selective fractions: 90% by GC. EIMS: m/z (%, major isomer); 186 (2), 185.9 (18), 184.8 (25), 183.9 (100), 182.9 (92), 181.9 (92), 181.9 (60), 180.9 (63), 179.9 (45), 178.9 (23), 168.8 (27), 166.9 (13).

Synthesis of Me$_2$Si(2-Methylhydrocyclopenta[1,2-b]selenopentalene)$_2$ (bridged ligand)

In a 200 mL flask containing 0.6 g (3.2 mmol) 5-methyl-4-hydrocyclopenta-[1,2,b]selenopentalene dissolved in 40 mL diethyl ether was added a solution of n-butyllithium (2.5M in hexane, 3.2 mmol, 1.3 mL) at room temperature dropwise. The flask contents were stirred for 1 h. A small amount of THF was added to dissolve the solids and facilitate the reaction.

In a separate 250-mL flask with 125-mL addition funnel was added 0.21 g (1.6 mmol) dichlorodimethylsilane dissolved in 40 mL THF. The solution was cooled to −78° C., and the solution containing the dianion prepared above was added dropwise. The flask contents were allowed to warm to room temperature then stirred for 18 h. The reaction mixture was quenched with 40 mL of a saturated solution of ammonium chloride (added dropwise). The organics from the reaction mixture were collected with diethyl ether, washed with water, dried over magnesium sulfate, filtered, then the solvents were removed in vacuo. 0.56 g dark orange oil was collected and chromatographed on silica using hexane as the eluent. 0.3 g product (50% by GCMS); EIMS: m/z: 426.9 (1), 425.8 (4), 424.8 (2), 423.8 (10), 422.8 (3), 421.8 (9), 242.9 (13), 241.9 (12), 240 (59), 239.9 (12), 238.9 (31), 237.9 (15), 236.9 (13), 160 (20), 159 (100), 157 (2).

Synthesis of Me$_2$Si(2-Methylhydrocyclopenta[1,2-b]selenopentalene)$_2$ Zirconium Dichloride In a 100 mL flask was placed 0.3 g (0.71 mmol) Me$_2$Si(2-methylhydrocyclopenta[1,2-b]selenopentalene)$_2$ dissolved in diethylether. Dropwise, a solution containing n-butyllithium was added (1.2 mL, 2.5M in hexane, 3 mmol). The reaction mixture was stirred for 20 min., the solvents were removed in vacuo. The solids were washed with pentane, then re-slurried in fresh pentane. 0.2 g (0.8 mmol) zirconium tetrachloride was added slowly to the stirred slurry as a dry powder. The reaction mixture was stirred overnight, then filtered, and the solids collected were washed with pentane. The solids were dissolved in diethylether, filtered, then the solvents removed in vacuo. 0.48 g was collected and used in subsequent polymerization studies. $^1$H-NMR (CD$_2$Cl$_2$): 7.0–7.4 (m, 6H), 2.38 (s, 6H), 0.5 (s, 6H).

EXAMPLE 6 (COMPARISON)

Dimethylsilandiylbis-4-(2,5-dimethyl-1-phenylcyclopentadienyl-[2,1-b]-pyrrol)zirconium Dichloride—{Me$_2$Si(2,5-Me$_2$-1-Ph-cyclopento[3,2-b]pyrrol-4-yl)$_2$}ZrCl$_2$ N1

This compound was prepared according to the procedure of Example 13 described in WO 98/22486.

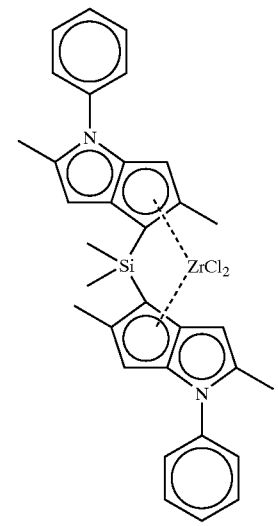

EXAMPLE 7 (COMPARISON)

Synthesis of Dimethylsilandiylbis-4-(3-methyl-1-phenylcyclopentadienyl-[2,1-b1-pyrrol)zirconium Dichloride {Me$_2$Si(5-Me-1-Ph-Cyclopento[3,2-b]pyrrol-4-yl)$_2$}ZrCl$_2$ N2

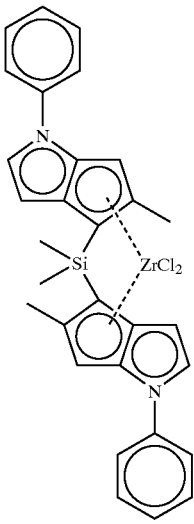

1-Phenylpyrrole-2-carbaldehyde

POCl$_3$ (107.3 g, 0.70 mol) was added dropwise to 76 mL of DMF (71.7 g, 0.98 mol) and stirred for 10 min. The temperature was lowered to 0° C. and a solution of 1-phenylpyrrole (100 g, 0.70 mol) in 100 mL of dichloromethane was added slowly. The viscous solution was slowly warmed to 50° C. and stirring continued for 1 h. After cooling to room temperature, the flask was opened to the air and charged with 750 g of crushed ice. A 20 wt % solution of NaOH (885 mL) was added cautiously and the mixture was immediately heated to 85–90° C. and stirred for 10 min. The solvent was distilled off in the process. The flask was placed in an ice bath, cooled to room temperature, and the reaction mixture was extracted with dichloromethane (2×200 mL). The combined organic fractions were washed with water and dried (MgSO$_4$). Evaporation of the solvent yielded 114 g of product as an orange oil containing ca. 10% of the 1-phenylpyrrole-3-carbaldehyde isomer. The product was used without further purification. $^1$H-NMR (CDCl$_3$): δ 9.5 (s, 1H), 7.4 (m, 3H), 7.3 (m, 2H), 7.1 (dd, 1H), 7.0 (t, 1H), 6.35 (dd, 1H). $^{13}$C-NMR δ (CDCl$_3$): 178.1, 138.1, 131.9, 130.4, 128.4, 127.5, 125.4, 121.3, 110.3. EIMS: m/z (%) 171 (M+, 100), 154 (7), 142 (8), 115 (50), 93 (42), 77 (16).

Ethyl[2Z]-2-Me-3-[1-phenylpyrrol-2-yl]prop-2-enoate

A solution of triethyl 2-phosphonopropionate (153 mL, 0.714 mol) in 75 mL of THF was added slowly to a mixture of sodium hydride (24.3 g, 1.0 mol) in 60 mL of THF at 0° C. The slurry was warmed to room temperature and stirred for 1 h. The temperature was lowered to –10° C. and a solution of 1-phenylpyrrole-2-carbaldehyde (113 g, 0.665 mol) in 200 mL of TBF was added dropwise. The reaction mixture was warmed to room temperature over 30 min. resulting in a thick precipitate. A saturated aqueous solution of NH$_4$Cl (100 mL) was added cautiously giving a two-phase solution. THF was distilled off and the crude product was extracted with ether (2×200 mL). The ether extract was washed with brine solution, and dried (MgSO$_4$). The solvent was evaporated and the crude product was washed with hexane to give the product as a white crystalline solid. Yield: 89% (151 g). $^1$H-NMR (CDCl$_3$): δ 7.4 (m, 4H), 7.3 (m, 2H), 7.0 (dd, 1H), 6.7 (dd, 1H), 6.4 (t, 1H), 4.1 (q, 2H), 2.2 (s, 3H), 1.2 (t, 3H). $^{13}$C-NMR δ (CDCl$_3$): 168.6, 139.0,129.4, 129.0, 127.3, 126.1, 126.0, 124.8, 122.8, 114.1, 109.9, 60.2, 14.1. EIMS: m/z (%) 255 (M+, 50), 226 (5), 210 (23), 182 (100), 167 (47), 154 (12), 115 (7), 77 (18). mp 73° C.

Ethyl 2-Me-3-[1-Phenylpyrrol-2-yl]propanoate

A mixture of ethyl[2Z]-2-Me-3-[1-phenylpyrrol-2-yl]prop-2-enoate (55 g, 0.22 mol) and 10% Pd/C (2.3 g) in 300 mL of dichloromethane was stirred under 80 psig of hydrogen for 4 h. After filtering off the catalyst and washing with dichloromethane, solvent was removed on a rotoevaporator to give the product. Yield: 54 g (97%). $^1$H-NMR (CDCl$_3$): δ 7.4 (m, 3H), 7.2 (m, 2H), 6.7 (m, 1H), 6.1 (m, 1H), 6.0 (m, 2H), 4.0 (q, 2H), 2.9 (m, 1H), 2.5 (m, 2H), 1.2 (t, 3H), 1.0 (d, 3H). $^{13}$C-NMR (CDCl$_3$): δ 175.6, 128.9, 127.0, 126.0, 121.8, 107.8, 60.0, 39.3, 30.3, 16.7, 13.9. EIMS: m/z (%) 257 (M+, 9), 216 (7), 184 (6), 146 (100), 77 (16).

2-Me-3-[1-Phenylpyrrol-2-yl]propanoic Acid

The ester ethyl 2-Me-3-[1-phenylpyrrol-2-yl]propanoate (42.1 g, 0.164 mol) was treated with 78 mL of Claisen's reagent and heated to 90–95° C. After stirring for 1 h, the solution was poured onto crushed ice and acidified to pH 1–2 with 6 N HCl. The precipitated free acid was extracted with ether (2×200 mL), washed with brine solution, and dried (MgSO$_4$). Ether was removed from the product by rotoevaporation. Yield: 27.9 g (75%). $^1$H-NMR (CDCl$_3$): δ 7.2–7.6 (m, 5H), 6.7 (d, 1H), 6.2 (t, 1H), 6.1 (d, 1H), 3.0(m, 1H), 2.6 (m, 2H), 1.1 (d, 3H).

5-Me-1-Ph-5,6-Dihydrocyclopenta[1,2-b]pyrrol-4-one

A solution of 2-Me-3-[1-phenylpyrrol-2-yl]propanoic acid (43 g, 0.188 mol) in 75mL of dichloroethane was added dropwise to 1000 g of super PPA at 100° C. After stirring for 5 h, the mixture was cooled to 60° C. and poured slowly onto crushed ice. The product was extracted with 30% (v/v) dichloromethane in hexane (2×200 mL). The combined organic fractions were washed with a saturated aqueous solution of NaHCO$_3$, and dried (MgSO$_4$). Solvents were removed on a rotoevaporator leaving the product as a tan solid. Yield: 37 g (93%). $^1$H-NMR (CDCl$_3$): δ 7.5 (m, 2H), 7.4 (m, 3H), 7.1 (d 1H), 6.4 (d, 1H), 3.3 (dd, 1H), 3.0 (m, 1H), 2.6 (dd, 1H), 1.3 (d, 3H). $^{13}$C-NMR (CDCl$_3$): δ 199.6, 156.6, 138.8, 129.8, 129.2, 127.9, 127.2, 122.0, 104.1, 47.5, 30.8, 17.1. EIMS: m/z (%) 211 (M+, 100), 196 (55), 182 (33), 167 (27), 154 (12), 120 (23), 105 (38), 77 (46). mp 120° C.

Tosylhydraazone of 5-Me-1-Ph-5,6-Dihydrocyclopenta[1,2-b]pyrrol-4-one

5-Me-1-Ph-5,6-dihydrocyclopenta[1,2-b]pyrrol-4-one (36 g, 0.171 mol), p-toluenesulfonhydrazide (33 g, 0.177 mol), and p-toluenesulfonic acid monohydrate (6.6 g, 0.035 mol) were stirred in 220 mL of ethanol at 70° C. for 16 h. After cooling to room temperature and standing for several hours, the precipitated product was collected on a filter funnel, washed with ether, and dried under vacuum. Solvents were evaporated from the filtrate and additional product was obtained by triteration of the residue with toluene. A tan solid was recovered. Yield: 58.9 g (91%). $^1$H-NMR (CDCl$_3$): δ 7.9 (d, 2H), 7.1–7.6 (m, 7H), 7.1 (d, 1H), 6.7 (d, 1H), 3.5 (m, 1H), 3.2 (dd, 1H), 2.6 (dd, 1H) 2.4 (s, 3H), 1.3 (d, 3H). $^{13}$C-NMR (CDCl$_3$): δ 162.2, 147.0, 143.5, 138.9, 135.5, 129.7, 129.2, 128.1, 126.9, 126.3, 121.8, 121.4, 105.5, 42.8, 32.4, 21.5, 19.7. mp 186° C. (dec).

5-Me-1-Ph-4-Hydrocyclotpenta[2,1-b]pyrrole

To a solution of the tosylhydrazone (32.5 g, 0.086 mol) in THF (200 mL) was added 76 mL of n-butyllithium in hexanes (2.5 M, 0.189 mol) at −78° C. The reaction mixture was slowly warmed to room temperature and stirred for 16 h. A saturated aqueous solution of $NH_4Cl$ (20 mL) was added dropwise and the organic solvents were distilled off. Water (100 mL) was added and the mixture was extracted with ether (2×100 mL). The combined ether fractions were dried ($MgSO_4$) and solvent removed on a rotoevaporator. The brown oily residue was stirred vigorously with hexane (150 mL) for 1 h. The insoluble products were removed by filtration and the hexane was evaporated giving the product as a light yellow oil. Yield: 12 g (72%). Two isomers—$^1$H-NMR ($CDCl_3$): δ 7.5 (m, 4H), 7.3 (m, 1H), 7.1 (d, 1H), 7.0 (d, 1H), 6.6 (s, 1H), 6.4 (s, 1H), 6.3 (d, 1H), 6.2 (d, 1H), 3.3 (s, 1H), 3.1 (s, 1H), 2.2 (s, 3H), 2.17 (s, 3H). EIMS: m/z (%) 195 ($M^+$, 100), 180 (28), 167 (7), 152 (10), 139 (2), 127 (3), 116 (3), 91 (12), 77 (8).

(5-Me-1-Ph-4-Hydrocyclotpenta[3,2-b]pyrrol-4-yl)$SiMe_2Cl$

A solution of 5-Me-1-Ph-4-hydrocyclopenta[2,1-b]pyrrole (11.2 g, 0.057 mol) in 100 mL of ether was treated with 28 mL of n-butyllithium in hexanes (2.5 M, 0.070 mol) at −10° C. and stirred at room temperature for 16 h. Pentane (50 mL) was added to the reaction mixture, the precipitated lithium salt was allowed to settle, and the liquid was removed with a filter stick. The precipitate was re-dissolved in ether (150 mL), cooled to −78° C., and dichlorodimethylsilane (10.5 mL, 0.086 mol) was added by syringe. The reaction mixture was warmed to room temperature and then refluxed for 2 h. After cooling and filtration, volatiles were removed from the filtrate in vacuo (100 millitorr, 40° C.) giving the product as a colorless oil. Yield: 12.7 g (77%). $^1$H-NMR ($CD_2Cl_2$): δ 7.5 (m, 4H), 7.3 (m, 1H), 7.0 (d, 1H), 6.6 (s, 1H), 6.3 (d, 1H), 3.3 (s, 1H), 2.3 (s, 3H), 0.5 (s, 3H) 0.1 (s, 3H). $^{13}$C-NMR ($CD_2Cl_2$): δ 144.9, 129.9, 125.5, 121.1, 120.6, 117.9, 106.2, 45.0, 18.0, 0.95, −1.25.

(5-Me-1-Ph-4-Hydrocyclopenta[3,2-b]pyrrol-4-yl)$_2SiMe_2$

A solution of of 5-Me-1-Ph-4-hydrocyclopenta[2,1-b]pyrrole (4.7 g, 24 mmol) in 60 mL of ether was treated with 11.2 mL of n-butyllithium in hexanes (2.5 M, 28 mmol) and stirred for 16 h. Pentane (50 mL) was added and the slurry was filtered through a closed frit funnel. The tan lithium salt was re-dissolved in 50 mL of THF, cooled to −78° C., and treated with (5-Me-1-Ph-4-hydrocyclopenta[3,2-b]pyrrol-4-yl)$SiMe_2Cl$ (6.7 g, 24 mmol) dissolved in 50 mL of THF. The dark brown solution was slowly warmed to 50° C. and stirred for 16 h. Volatiles were removed in vacuo and the residue was extracted with dichloromethane to remove LiCl. Evaporation of the solvent gave the product as a white solid. Yield: 8.5 g, (81%). Two isomers—$^1$H-NMR ($CD_2Cl_2$): δ 7.5 (m, 8H), 7.25 (m, 2H), 7.05 (d, 1H), 6.95 (d, 1H), 6.6 (s, 2H), 6.5 (d, 1H), 6.3 (d, 1H), 3.45 (s, 2H), 2.3 (s, 3H), 2.2 (s, 3H), −0.20 (s, 3H), −0.22 (s, 3H). $^{13}$C-NMR ($CD_2Cl_2$): δ 146.3, 146.2, 141.3, 140.7, 130.3, 129.9, 125.2, 120.9, 120.2, 120.1, 117.0, 106.4, 106.2, 42.8, 42.5, 18.3, 18.25, −6.9, −7.2. EIMS: m/z (%) 446 ($M^+$, 18), 252 (100), 237 (8), 224 (7), 194 (7), 165 (3).

{$Me_2Si$(5-Me-1-Ph-Cyclopento[3,2-b]pyrrol-4-yl)$_2ZrCl_2$

A solution of (5-Me-1-Ph-4-hydrocyclopenta[3,2-b]pyrrol-4-yl)$_2SiMe_2$ (4.0 g, 9.0 mmol) in 100 mL of ether was cooled to −78° C., treated with 8.0 mL of butyllithium in hexanes (2.5 M, 20 mmol), and warmed to room temperature. After stirring overnight, the pressure was reduced to evaporate the solvents. The residue was washed with pentane (40 mL) and dried in vacuo to a free flowing tan powder. $ZrCl_4$ (2.09 g, 9.0 mmol) was added to the flask and the contents were stirred overnight in a mixture of pentane (75 mL) and ether (1.5 mL). The solids were collected on a closed frit funnel, washed with pentane, and dried under vacuum giving an orange solid (5.9 g). A portion of the crude product (5.65 g) was stirred in dichloromethane (75 mL) and filtered. The filtrate was concentrated to a small volume and pentane was added to precipitate the complex. Yield: 4.1 g (79%, 50/50 rac/meso). Crystals of the rac isomer were obtained by slow evaporation of a dichloromethane/toluene solution of the rac/meso complex. $^1$H-NMR ($CD_2Cl_2$): δ 7.3–7.5 (m, 8H, rac & meso), 7.38 (d, j=3.5 Hz, 2H rac), 7.15–7.25 (m, 2H, rac & meso), 7.12 (d, j=3.5 Hz, 2H, meso), 6.45 (s, 2H, rac), 6.4 (s, 2H, meso), 6.32 (d, j=3.5 Hz, 2H, rac), 6.2 (d, j=3.5 Hz, 2H, meso), 2.4 (s, 6H, meso), 2.2 (s, 6H, rac), 1.125 (s, 3H, meso), 1.118 (s, 3H, meso), 1.10 (s, 6H, rac). Anal. Calcd for $C_{30}H_{28}Cl_2N_2SiZr$: C, 59.38; H, 4.65. Found: C, 59.78; H, 4.74.

POLYMERIZATIONS

General Procedures and Characterizations

Polymerization grade propylene was purchased from the Matheson Gas Co. and further purified by passing through columns of 3 angstrom molecular sieves and alumina. Methylalumoxane (toluene solution, 10% MAO, 4.92% Al) was purchased from Witco Corp. and used as received. Al(iBu)$_3$ (24.5% sol. in heptane) was purchased from Akzo Nobel Chemicals. [$CPh_3$][$B(C_6F_5)_4$] was received from Asahi Glass Co.

NMR

For polymer NMR analyses, the solution $^{13}$C-NMR spectra were run at 75.4 MHz on a Varian UNITY-300 NMR spectrometer. The samples were run as 10% (w/v) solutions in orthodichlorobenzene-$d_4$ at 130° C. Chemical shifts are referenced to TMS using a secondary reference, the $CH_3$ methyl peak of polypropylene at 21.8 ppm. 5000 transients were accumulated for each spectrum with a 10-second delay between pulses. Decoupling was always on during acquisition so the nuclear Overhauser enhancement was present.

Solution intrinsic viscosity $[\eta]_o$ of polymer samples were determined in Decalin at 135° C. The intrinsic viscosities were converted to weight average molecular mass ($M_w$) by gel permeation chromatography (GPC) using an empirical correlation of $M_w$ and $[\eta]_o$ for metallocene catalyzed polypropylene homopolymers ($log_{10}[\eta]_o$=−3.8996+ (0.7748*$log_{10}${$M_w$}).

For example 49–56 the NMR carbon spectra were acquired on a Bruker DPX-400 spectrometer operating in the Fourier transform mode at 120° C. at 100.61 MHz. The samples were dissolved in $C_2D_2Cl_4$ with a concentration of 8% w/v.

The spectra were acquired with a 90° pulse and 15 seconds of delay between pulses. About 1500 (or 3000 for polypropylene and polybutene) transients were stored for each spectrum.

The peak of the PPP methyl carbon or of the $CH_2$ branch for polybutene were used as internal reference at 21.80 ppm and 27.73 ppm respectively. Assignments are according to H. N. Cheng, *J. Polym. Science: Polymer physics edition* 21, 573 (1983) and J. C. Randall, *Macromolecules* 11, 592 (1978).

The intrinsic viscosity (I.V.)

The intrinsic viscosities were converted to weight average molecular weight by GPC ($M_w$) using an empirical correlation of $M_w$ and $[\eta]_o$ for metallocene catalyzed polypropylene homopolymers.

DSC

Transition temperature and enthalpy of melting and crystallization of polymer samples were measured using a power-compensation mode Perkin Elmer (PE) DSC-7 and PE PYRIS (revision 3.03) software. A PE Intercooler II (Model FC100PEA) was used for cooling. The instrument was calibrated against certified (1) indium with Teim= 156.60° C.; $H_f$=28.71 J/g and (2) tin with Teim 231.88° C.; Hf=60.46 J/g. The dynamic heating /cooling rate was 20° C./min. The purge gas was nitrogen flowing at 20±2 cc/min. A three ramp (heat-cool-reheat) procedure was employed with upper and lower temperature limits of 25° C. and 235° C., respectively. The isothermal hold time between ramps was 3 minutes. The results of the second heat are reported.

GPC Analysis (for examples 41–48): High temperature GPC analyses were performed using the following chromatographic conditions:

| | |
|---|---|
| Column: | PLgel 2 x mixed bed-B, 30 cm, 10 microns |
| Solvent: | 1,2-dichlorobenzene with antioxidant |
| Flow rate: | 1.0 ml/min |
| Temperature: | 140° C. |
| Detector: | refractive index |
| Calibration: | polystyrene |

EXAMPLE 8 TO 31

The polymerizations were conducted in a 4 l stainless reactor equipped with an air-driven magnetic stirrer and steam/water temperature controlled jacket. The autoclave was swept with dry argon at 90° C. for 1 h prior to polymerization. The zirconocene was dissolved in a 10 wt % toluene solution of MAO, shaken for 10 minutes, and added to the reactor at 15° C. Propylene (2.2 L) was added, stirring was initiated (500 rpm), and the reactor and contents were heated to the polymerization temperature within 5–7 minutes. In all polymerization tests, carbon monoxide gas was charged to the reactor 1 h after reaching polymerization temperature. The residual monomer was vented while cooling the reactor to room temperature. The polymer was removed and dried in a vacuum oven at 50° C. for 1 h before weighing. Reported activities were calculated from polymer and zirconocene weights. The characterizing data of the obtained polymer is indicated in Table 1.

EXAMPLES 32 TO 34 (COMPARISON)

The same polymerization as described above was carried out, using metallocenes as shown in Table 1. The characterizing data of the obtained polymer is indicated in Table 1.

EXAMPLE 35

The polymerization was conducted in a 4 L stainless steel reactor equipped with an air-driven magnetic stirrer and steam/water temperature controlled jacket. The autoclave was swept with dry argon at 90° C. for 1 h prior to polymerization. C3 (0.05 mg) was dissolved in a 10 wt % solution of MAO in toluene (10 mL), shaken for 10 minutes, and transferred to a stainless steel sample bomb attached to the reactor. Propene (2.2 L) was added to the cooled reactor (20° C.) and stirring was initiated (500 rpm). The catalyst was charged to the reactor with ethene gas to 100 psi-g above the vapor pressure of propene in the reactor. The reactor and contents were heated to 50° C. within 5–7 minutes and the ethene feed was adjusted to maintain 100 psi-g overpressure above the vapor pressure of propene. After 1 h, carbon monoxide gas was charged to the reactor to terminate the run and residual monomer was vented. The reactor was cooled to room temperature, and swept with a stream of argon for several minutes before opening. The polymer was removed and dried in a vacuum oven at 80° C. for 1 h before weighing. Yield—254 g of polymer (19.9 wt % ethene by IR analysis).

EXAMPLES 36–40

The polymerizations were conducted in a 4 l stainless reactor equipped with an air-driven magnetic stirrer and steam/water temperature controlled jacket. The autoclave was swept with dry argon at 90° C. for 1 h prior to polymerization. A toluene solution of the zirconocene and Al(iBu)$_3$ was added to the reactor at 15° C. followed by 2.2 L of propylene. Stirring was initiated (500 rpm), a toluene solution of [CPh$_3$][B(C$_6$F$_5$)$_4$] was charged to the reactor with 100 mL of propane, and the contents were heated to the polymerization temperature within 5–7 minutes. In all polymerization tests, carbon monoxide gas was charged to the reactor 1 h after reaching polymerization temperature. The residual monomer was vented while cooling the reactor to room temperature. The polymer was removed and dried in a vacuum oven at 50° C. for 1 h before weighing. Reported activities were calculated from polymer and zirconocene weights. The characterizing data of the obtained polymer is indicated in Table 2.

EXAMPLE 41

A 5 liters reactor equipped with turbine stirrer, steam/water temperature control and a catalyst injection system was heated to 150–160° C. overnight, whilst purging with nitrogen, cooled and then pickled at 70° C. using a mixture of TIBA (0.25 g), toluene (20 ml) and propylene (500 g). The pickle mixture was removed and the reactor then charged with 1650 g liquid propylene, whilst increasing the temperature from 20° C. to 30° C. Then 4–5% hydrogen was added to the gascap, aiming at 1–1.5% hydrogen in the gascap at 70° C. Two minutes after adding hydrogen 1 mmol TIBA (198 mg) was injected into the reactor using 20 ml toluene.

Separately, 2.00 g of tris{2-phenyl-propyl} Al[CH$_2$CHMe (C$_6$H$_5$)]$_3$ (5.20 mmol) was dissolved in 20.0 g of toluene in a bottle with a septum cap. The solution was cooled to 0–4° C. using an ice bath, and 47 microliter of water (2.61 mmol) added in two shots using a 100 microliter syringe, whilst maintaining the temperature below 15° C.

Meanwhile, 13.1 mg of rac-C3 (19.4 micromol) was dissolved in 23.3 g of toluene, and 0.717 g of the obtained solution containing 0.75 micromol zirconium complex was reacted with 28 mg TIOA (76.5 micromol), resulting in a color change from yellow to light yellow. After 5 minutes 1.59 g of the hydrolyzed alkylaluminium mixture containing 0.38 mmol aluminoxane was added to this solution. Twenty minutes after the introduction of TIBA into the reactor, the alkylated zirconocene solution (aged for 5 minutes) was injected into the reactor (using 20 ml toluene) at a temperature of 30° C. After 0.5 minute the temperature was raised in 6–7 minutes to 70° C. and polymerization was continued for 1 hour, using 840–1100 rpm stirring, keeping the hydrogen concentration at 1% in the gascap. The polymerization was then stopped by injection of 5–10 ml methanol. The heating was then discontinued and the propylene rapidly vented and the powder polypropylene collected. Fouled material was removed using hot xylene and precipitated with methanol. The polypropylene fractions were dried (70–80° C., 200 mbar, nitrogen purge) and combined to give the total yield of polypropylene. The polymerization conditions and the data related to the obtained polymers are indicated in Table 3.

EXAMPLE 42

The experiment was performed similarly to example 39 but using the aluminoxane obtained from the reaction of tris{2,3-dimethyl-butyl}aluminum Al[$CH_2CHMeCHMe_2$]$_3$ with water. Catalyst rac-C3 (0.72 micromol), pretreated with TIOA (76.5 micromol), followed by the aluminoxane (0.38 mmol), was added to the reactor containing TIBA scavenger (1 mmol). The polymerization conditions and the data related to the obtained polymers are indicated in Table 3.

EXAMPLE 43

A 5 liters reactor equipped with turbine stirrer, steam/water temperature control and a catalyst injection system was heated to 150–160° C. overnight, whilst purging with nitrogen, cooled and then pickled at 70° C. using a mixture of TIBA (0.25 g), toluene (20 ml) and propylene (500 g). The pickle mixture was removed and the reactor then charged with 1650 g liquid propylene, whilst increasing the temperature from 20° C. to 30° C. Then 4–5% hydrogen was added to the gascap, aiming at 1–1.5% hydrogen in the gascap at 70° C.

Separately, 1.98 g of tris{2-(p-fluorophenyl)-propyl} Al[$CH_2CHMe(4-F-C_6H_4)$]$_3$ 4.5 mmol) were dissolved in 20 ml of toluene in a bottle with a septum cap. The solution was cooled to 0–4° C. using an ice bath, and 41 microliter of water (2.28 mmol) added in two shots using a 100 microliter syringe, whilst maintaining the temperature below 15° C. The resulting solution was introduced into the reactor using an injection system, washed in using 20 ml of toluene.

Meanwhile, 13.3 mg of rac-C4 (19 micromol) was dissolved in 24.34 g of toluene, and 0.304 g of the obtained solution containing 0.24 micromol zirconium complex was reacted with 0.11 g TIOA (0.3 mmol), resulting in a color change from yellow to light yellow. Ten minutes after the introduction of the hydrolyzed alkylaluminium mixture containing 4.5 mmol aluminoxane into the reactor, the alkylated zirconocene solution (aged for 5 minutes) was injected into the reactor (using 20 ml toluene) at a temperature of 30° C. After 0.5 minute the temperature was raised in 6–7 minutes to 70° C. and polymerization was continued for 26 minutes, using 840–1100 rpm stirring, keeping the hydrogen concentration at 1% in the gascap. The polymerization was then stopped by injection of 5–10 ml methanol. The heating was then discontinued and the propylene rapidly vented and the powder polypropylene collected. Fouled material was removed using hot xylene and precipitated with methanol. The polypropylene fractions were dried (70–80° C., 200 mbar, nitrogen purge) and combined to give the total yield of polypropylene. The polymerization conditions and the data related to the obtained polymers are indicated in Table 3.

EXAMPLE 44

The experiment was performed similarly to example 41 but using the aluminoxane obtained from the reaction of tris(2,3-dimethyl-butyl}aluminum Al[$CH_2CHMe(4-F-C_6H_4)$]$_3$ with water. Catalyst rac-C4 (0.72 micromol), pretreated with TIOA (76.5 micromol), followed by the aluminoxane (0.38 mmol), was added to the reactor containing TIBA scavenger (1 mmol). The product yield and properties are given in Table 3. The polymerization conditions and the data related to the obtained polymers are indicated in Table 3.

EXAMPLE 45

This polymerization example was carried out as example 41 excepting that compound C5 is used instead of compound C4.

EXAMPLE 46

This polymerization example was carried out as example 42 excepting that compound C5 is used instead of compound C4.

EXAMPLE 47

This polymerization example was carried out as example 42 excepting that compound C5 is used instead of compound C4 and the aluminum/zirconium ratio was 250.

EXAMPLE 48

This polymerization example was carried out as example 42 excepting that compound C5 is used instead of compound C4 and MAO was used instead of TFPPA.

EXAMPLE 49

Preparation of a Supported Catalyst System Containing C3 and MAO Supported on Polyethylene Polymer (PE)

Carrier

For the preparation of supported catalyst A and B a PE polymer with the following physical properties was used:

mean particle size 151 μm porosity 0.357 cc/g (24.2% V/V)

surface area 1.4 m$^2$/g mean pore diameter 1.5 μm

Supportation Apparatus

The apparatus for the supportation of the catalyst consists of two zones. The first zone containing an impregnation column equipped with a mechanical device in which the catalytic solution is continuously fed and that contains the prepolymer to be impregnated and a second zone heated for evaporating the solvent. In the semicontinuous process, after loading the carrier, the catalytic solution is continuously fed to the prepolymer into an impregnation column from which the impregnated prepolymer is pneumatically conveyed through the zone for the evaporation of the solvent and then recirculated again to the first zone after separation from the gas stream by means of a cyclone (described in "Perry's chemical engineers' handbook" sixth edition page 18–73). The two zones of the loop reactor are jacketed and maintained at different temperature to optimize the operation that takes place in each zone, impregnation or evaporation. The impregnation column is stirred in order to allow a fast and homogeneous absorption of the catalytic solution.

Preparation of Catalyst A 40.8 g of PE prepolymer was loaded in the equipment described above and the jacket temperature of the impregnation column and the flashing zone was respectively set to 45 and 90° C. The recirculation of the solid in the loop reactor was initiated by flowing nitrogen through the flashing column. Once the set temperature was reached in the two zones, 20 mL of a 100 g/L MAO solution in toluene (WITCO) was dosed in 15 minutes using a dosing pump. This initial amount of MAO reacts with the residual water present in the support (typically 300–400 ppm) avoiding that the active catalyst is destroyed during supportation. The catalytic solution was prepared under nitrogen by dissolving 173 mg of C3 in 60 mL of the MAO solution. The bright orange catalytic solution was dosed onto the carrier in 1 hour. The impregnated support was then recirculated for 15 minutes without adding any other components to eliminate the last traces of solvent. The analysis of the discharged supported catalyst is 5.75% w Al and 470 ppm Zr with an Al/Zr molar ratio of 412.

Preparation of Catalyst B 43.7 g of PE prepolymer was loaded into the apparatus and the internal temperature raised up to the desired values (the same as for the previous preparation) while recirculating the solid in the loop reactor. Also for this preparation the total amount of MAO solution added to the carrier was 80 mL, but it was split in 3 consecutive addition steps: first 15 mL to scavenge the residual water present onto the carrier, then 50 ml in the precontact solution (obtained dissolving 180 mg of C3) and the last 15 mL of MAO alone after having fed the whole catalytic solution. The three solutions were dosed to the support in 1.5 hours using a constant feeding rate. Before discharging the supported catalyst the solid was maintained in recirculation for 15 minutes to completely dry it. The composition of the final catalyst is 6.5% w Al, 407 ppm Zr with a Al/Zr molar ratio of 538.

EXAMPLES 50–53

Copolymerization of Propylene and 1-Butene With Supported C3/MAO Catalyst 4 mL of a 0.5 M hexane solution of TIBA (2 mmol) and the amounts of propylene and butene detailed in Table 4 (corresponding to 2.5 L of liquid monomers at 70° C.) were loaded into a 4.25-L stainless-steel stirred reactor at 30° C. The solid catalyst (see Table 4) was then injected into the reactor by means of nitrogen overpressure through a stainless-steel vial, which was then rinsed with 5 mL of hexane, and then the temperature of the reactor was raised to 70° C. in 10 min. The polymerization was carried out at 70° C. for 60 min, then stopped with 1 L of CO, and finally the reactor was vented and cooled, and the free-flowing, spherical product was collected and dried (vacuum oven, 2 h, 70° C.).

Catalyst activity and characteristics of the obtained polymers are summarized in Table 4.

EXAMPLE 54

Polymerization of 1-Butene With Supported C3/MAO Catalyst 4 mL of a 0.5 M hexane solution of TIBA (2 mmol) and 850 g of 1-butene were loaded into a 4.25-L stainless-steel stirred reactor at 30° C. The solid catalyst B (266 mg) was then injected into the reactor by means of nitrogen overpressure through a stainless-steel vial, which was then rinsed with 5 mL of hexane, and then the temperature of the reactor was raised to 70° C. in 10 min. The polymerization was carried out at 70° C. for 60 min, then stopped with 1 L of CO, and finally the reactor was vented and cooled. 7 g of isotactic polybutene were collected and dried (vacuum oven, 2 h, 70° C.). This product has I.V. 1.12 dl/g, Tm=101° C. ?H=82 J/g.

EXAMPLES 55–57

Copolymerization of Propylene and Ethylene With Supported C3/MAO Catalyst 4 mL of a 0.5 M hexane solution of TIBA (2 mmol) and the amounts of propylene detailed in Table 5 (corresponding to 3 L of liquid monomers at 70° C.) were loaded into a 4.25-L stainless-steel stirred reactor at 30° C. The solid catalyst (see Table 5) was then injected into the reactor by means of nitrogen overpressure through a stainless-steel vial, which was then rinsed with 5 mL of hexane, and then the temperature of the reactor was raised to the polymerization temperature in 10 min. Ethylene was fed by maintaining a constant overpressure throughout the polymerization tests. The polymerization was carried out for 60 min at constant temperature, then stopped with 1 L of CO, and finally the reactor was vented and cooled, and the free-flowing, spherical product was collected and dried (vacuum oven, 2 h, 70° C.).

Catalyst activity and characteristics of the obtained polymers are summarized in Table 5.

TABLE 1

| | Bulk propene polymerization results with alumoxane cocatalyst | | | | | | | | | |
|---|---|---|---|---|---|---|---|---|---|---|
| Ex. | Zirconocene (mg) | MAO (10%) mL | $T_p$, °C. | $H_2$,a) Mmol | Yield, g | Activity, Kg/g-cat/h | $T_m$, °C. | IV, DL/g | $P_{2,1}$, Mol % | mrrm, mol % |
| 8 | C3 (0.20) | 10 | 50 | 0 | 212 | 1060 | 160 | 3.9 | n.d. | n.d. |
| 9 | C3 (0.05) | 10 | 50 | 55 | 399 | 7980 | 157 | 2.7 | n.d. | n.d. |
| 10 | C3 (0.05) | 10 | 70 | 0 | 146 | 2920 | 156 | 3.0 | 0.54 | 0.40 |
| 11 | C3 (0.05) | 10 | 70 | 55 | 513 | 10260 | 155 | 2.2 | n.d. | n.d. |
| 12 | C3 (0.05) | 10 | 70 | 55 | 516 | 10320 | 156 | 1.3 | n.d. | n.d. |
| 13 | C3 (0.05) | 5 | 70 | 55 | 374 | 7480 | 157 | 1.1 | 0.25 | 0.43 |
| 14 | C4 (0.05) | 5 | 50 | 55 | 155 | 3100 | 160 | 1.4 | n.d. | n.d. |
| 15 | C4 (0.10) | 5 | 50 | 0 | 74 | 740 | 161 | 5.8 | n.d. | n.d. |
| 16 | C4 (0.05) | 5 | 50 | 55 | 155 | 3100 | 161 | 1.8 | n.d. | n.d. |
| 17 | C4 (0.10) | 5 | 70 | 0 | 122 | 1220 | 160 | 3.4 | n.d. | n.d. |
| 18 | C4 (0.05) | 5 | 70 | 55 | 334 | 6680 | 157 | 1.4 | n.d. | n.d. |
| 19 | C4 (0.05) | 5 | 70 | 55 | 238 | 4760 | 160 | 1.5 | n.d. | n.d. |
| 20 | C4 (0.20) | 10 | 50 | 0 | 46 | 230 | 159 | 5.3 | n.d. | n.d. |
| 21 | C4 (0.20) | 10 | 50 | 55 | 418 | 2,090 | 160 | 3.3 | n.d. | n.d. |
| 22 | C4 (0.20) | 10 | 70 | 0 | 144 | 720 | 160 | 3.3 | 0.21 | 0.37 |
| 23 | C4 (0.10) | 10 | 70 | 55 | 522 | 5220 | 159 | 1.7 | n.d. | n.d. |

TABLE 1-continued

Bulk propene polymerization results with alumoxane cocatalyst

| Ex. | Zirconocene (mg) | MAO (10%) mL | $T_p$, °C. | $H_2$,[a] Mmol | Yield, g | Activity, Kg/g-cat/h | $T_m$, °C. | IV, DL/g | $P_{2,1}$, Mol % | mrrm, mol % |
|---|---|---|---|---|---|---|---|---|---|---|
| 24 | C5 (0.10) | 5 | 50 | 55 | 136 | 1360 | 163 | 1.9 | n.d. | n.d. |
| 25 | C5 (0.20) | 5 | 50 | 0 | 77 | 385 | 162 | 7.3 | n.d. | n.d. |
| 26 | C5 (0.10) | 5 | 50 | 55 | 94 | 940 | 162 | 2.6 | n.d. | n.d. |
| 27 | C5 (0.40) | 5 | 70 | 0 | 105 | 262.5 | 160 | 5.5 | 0.27 | 0.26 |
| 28 | C5 (0.10) | 5 | 70 | 55 | 419 | 4190 | 161 | 1.4 | 0.24 | 0.21 |
| 29 | C5 (0.10) | 5 | 70 | 55 | 188 | 1880 | 161 | 2.2 | n.d. | n.d. |
| 30 | C5 (0.20) | 5 | 70 | 0 | 132 | 660 | 160 | 4.7 | n.d. | n.d. |
| 31 | C6 (0.40) | 10 | 50 | 0 | 100 | 250 | 149 | 1.9 | n.d. | n.d. |
| 32 (comp) | N1 (0.40) | 10 | 50 | 0 | 35 | 88 | 155 | 1.7 | n.d. | n.d. |
| 33 (comp) | N1 (0.40) | 10 | 70 | 0 | 102 | 255 | 152 | 1.0 | 0.09 | 1.43 |
| 34 (comp) | N2 (0.40) | 10 | 50 | 0 | 146 | 730 | 146 | 1.26 | n.d. | 2.1 |

[a] mmol of hydrogen added to the reactor.
n.d. not determined
N1: 50/50 rac/meso — {Me$_2$Si(2,5-Me$_2$-1-Ph-cyclopento[3,2-b]pyrrol-4-yl)$_2$}.ZrCl$_2$
N2: 50/50 rac/meso — {Me$_2$Si(5-Me-1-Ph-cyclopento[3,2-b]pyrrol-4-yl)$_2$}ZrCl$_2$

TABLE 2

Bulk propene polymerization results with boron cocatalyst

| EX | Cocat[b] Mg | Catalyst Mg | Al(iBu)$_3$ Mmol | $H_2$[a] Mmol | T C | Yield G | Activity Kg.g-met-h | IV-DEc dL/g | DSC Tm C. ° | P-2,1 Mol % | mrrm mol % |
|---|---|---|---|---|---|---|---|---|---|---|---|
| 36 | 1.4 | C3 (0.10) | 1 | 10 | 70 | 314 | 3140 | 3.2 | 160 | 0.15 | 0.39 |
| 37 | 1.4 | C4 (0.20) | 1 | 0 | 70 | 126 | 630 | 5.5 | 162 | — | — |
| 38 | 1.4 | C4 (0.10) | 1 | 10 | 70 | 93 | 930 | 3.1 | 164 | 0.09 | 0.06 |
| 39 | 1.3 | C4 (0.10) | 1 | 10 | 50 | 77 | 770 | 3.8 | 165 | — | — |
| 40 | 1.2 | C3 (0.20) | 1 | 0 | 70 | 205 | 1025 | 3.6 | 157 | — | — |

[a] mmol of hydrogen added to the reactor;
[b] [Ph3C][B(C6F5)4].

TABLE 3 propene polymerization

| Ex | Catalyst | μmol | Cocatalyst precursor | Al/Zr (aluminoxane) | Yield g | Time (min) | Activity tons PP/g Zr.h | $M_w$ | $M_n$ | I.V. dl/g | Regioerrors (% 2,1- & 1,3) | mmmm % | mrrm % | Tm2* °C. | ΔH J/g* | XS % |
|---|---|---|---|---|---|---|---|---|---|---|---|---|---|---|---|---|
| 41 | C3 | 0.72 | AK | 530 | 19 | 60 | 0.29 | 54.2 | 26.9 | 0.54 | 0.21 | 96.3 | 0.4 | 156.4 | 112.5 | 1.4 |
| 42 | C3 | 0.72 | Q | 520 | 80 | 60 | 1.22 | 73.8 | 36.5 | 0.74 | 0.32 | 96.6 | 0.4 | 157.1 | 102.0 | 0.7 |
| 43 | C4 | 0.24 | AO | 18970 | 315 | 26 | 33.5 | 89.6 | 35.1 | 0.85 | 0.29 | 96.9 | 0.3 | 156.2 | 108.1 | 1.22 |
| 44 | C4 | 0.72 | AO | 530 | 270 | 60 | 4.14 | 73.3 | 28.0 | 0.75 | 0.27 | 95.6 | 0.4 | 156.6 | 105.2 | 2.4 |
| 45 | C5 | 0.25 | AK | 18020 | 568 | 29 | 51.5 | 68.5 | 30.2 | — | 0.23 | 97.7 | 0.2 | 159.6 | 111.1 | — |
| 46 | C5 | 0.5 | AO | 500 | 226 | 21 | 14.2 | 93.8 | 39 | — | 0.16 | 96.6 | 0.3 | 161.3 | 109.2 | — |
| 47 | C5 | 0.5 | AO | 250 | 183 | 60 | 4.0 | 62.8 | 17 | — | 0.17 | 94.8 | 0.4 | 160.1 | 109.9 | — |
| 48 | C5 | 0.5 | MAO | 500 | 341 (calc) | 60 | 7.5 | 105 | 32 | — | 0.21 | 98.0 | 0.2 | 161.7 | 110.3 | — |

TABLE 4 copolymerization of propylene and 1-butene with supported C3/MAO catalyst

| EXAMPLE | 50 | 51 | 52 | 53 |
|---|---|---|---|---|
| (gC3 + gC4)tot | 1129 + 52 | 1000 + 78 | 1000 + 134 | 1000 + 196 |
| (gC3 + gC4)liq | 1005 + 48.4 | 968 + 76.5 | 942 + 130 | 907 + 186 |
| Catalyst | B | A | A | B |
| Mg | 191 | 226 | 259 | 570 |
| kg/(gxh) | 1.47 | 0.93 | 0.52 | 0.72 |
| I.V. | 1.82 | 1.87 | 1.77 | 1.62 |
| $T_m$ | 141 | 137 | 134 | 119 |
| ?H | 92 | 89 | 88 | 78 |
| 2,1 (NMR) | 0.5 | 0.5 | 0.5 | n.d. |
| XS wt % | — | — | 1.4 | — |
| Comon. wt % (NMR) | 3.5 | 5.7 | 7.5 | 14.0 | a) 4,1 insertion only

TABLE 5 copolymerization of propylene and ethylene with supported C3/MAO catalyst.

| EXAMPLE | 55 | 56 | 57 |
|---|---|---|---|
| $(gC_3)_{tot}$ | 1289 | 1281 | 1367 |
| $(gC_3)_{liq}$ | 1192 | 1184 | 1294 |
| $\Delta P_{ethylene}$, bar | 0.5 | 1.0 | 0.9 |
| $(gC_2)_{calc,liqphase}$ | 6.1 | 12.1 | 13.1 |
| Catalyst | A | A | B |
| Mg | 228 | 213 | 350 |
| $T_p$ | 70 | 70 | 60 |
| Kg/(gxh) | 1.8 | 2.3 | 1.55 |
| I.V. | 1.62 | 1.31 | 1.32 |
| Comon. wt % (NMR) | 0.7 | 1 | 0.6 |

What is claimed is:

1. A metallocene compound of the general formula (I):

$$L \underset{Z}{\overset{Y}{\diagdown}} MX_p \quad (I)$$

wherein

Y is a moiety of formula (II)

$$(II)$$

wherein

A, B and D, same or different from each other, are selected from an element of the groups 14 to 16 of the Periodic Table of the Elements (new IUPAC version), with the exclusion of nitrogen and oxygen;

$R^1$, $R^2$, $R^3$, $R^4$ and $R^5$, same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical optionally containing heteroatoms belonging to groups 13–17 of the Periodic Table of the Elements; wherein two $R^3$ can form a ring comprising 4 to 8 atoms, or $R^3$ and $R^4$ can form a ring comprising 4 to 8 atoms, which can bear substituents; with the proviso that when s is 0 or when $R^3$ is hydrogen, $R^2$ is not hydrogen;

n, m and s, equal to or different from each other, are selected from 0, 1 and 2;

m, n and s being 0 when respectively A, B and D are selected from an element of the group 16 of the Periodic Table of the Elements (new IUPAC version);

m, n and s being 1 when respectively A, B and D are selected from an element of the group 15 of the Periodic Table of the Elements (new IUPAC version);

m, n and s being 1 or 2 when respectively A, B and D are selected from an element of the group 14 of the Periodic Table of the Elements (new IUPAC version);

and wherein the ring containing A, B and D can have double bonds in any of the allowed positions;

Z is selected from a moiety of formula (II) as described above and from a moiety of formula (III):

$$(III)$$

wherein $R^6$, $R^7$, $R^8$ and $R^9$, same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13–17 of the Periodic Table of the Elements, $R^7$ being different from hydrogen; optionally $R^6$ and $R^7$ or $R^7$ and $R^8$ can form a ring comprising 4 to 8 carbon atoms, which can bear substituents;

and when Z is a moiety of formula (II), Y and Z can be the same or different from each other;

L is a divalent bridging group;

M is an atom of a transition metal selected from those belonging to group 3, 4, 5, 6 or to the lanthanide or actinide groups in the Periodic Table of the Elements (new IUPAC version), X, same or different, is a hydrogen atom, a halogen atom, a $R^{10}$, $OR^{10}$, $OSO_2CF_3$, $OCOR^{10}$, $SR^{10}$, $NR^{10}_2$ or $PR^{10}_2$ group, wherein the substituents $R^{10}$ are selected from the group consisting of $C_1$–$C_{20}$ alkyl, $C_3$–$C_{20}$ cycloalkl, $C_6$–$C_{20}$ aryl, $C_7$–$C_{20}$ alkylaryl and $C_7$–$C_{20}$ arylalkyl radical, optionally containing heteroatoms belonging to groups 13–17 of the Periodic Table of the Elements;

p is an integer of from 1 to 3, being equal to the oxidation state of the metal M minus 2.

2. The metallocene compound according to claim 1, wherein the transition metal M is selected from titanium, zirconium and hafnium.

3. The metallocene compound according to claim 1, wherein X equal to or different from each other, are chlorine atoms or methyl groups or benzyl groups.

4. The metallocene according to claim 1, wherein L is $>Si(R^{17})_2$ or $>C(R^{17})_2$, wherein $R_{17}$, equal or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-arylalkyl radical, optionally containing heteroatoms belonging to groups 13–17 of the Periodic Table of the Elements, optionally two R can form a cycle comprising from 3 to 8 atoms that can bear substituents.

5. The metallocene according to claim 4, wherein L is selected from the group consisting of >Si($CH_3$)$_2$, >Si($C_6H_5$)$_2$, >$CH_2$ and >C($CH_3$)$_2$.

6. The metallocene according to claim 1, wherein A is selected from sulfur, selenium, tellurium and polonium and B and D are selected from the group 14 of the Periodic Table of the Elements (IUPAC version).

7. The metallocene according to claim 6, wherein A is sulfur and B and D are carbon atoms.

8. The metallocene compound according to claim 1, wherein Z is moiety of the formula (IV):

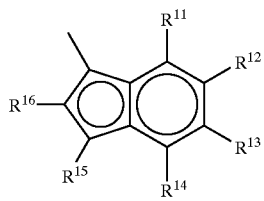

(IV)

wherein
$R^{11}$, $R^{12}$, $R^{13}$, $R^{14}$, $R^{15}$ and $R^{16}$, same or different from each other, are selected from hydrogen a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-arylalkyl radical, optionally containing heteroatoms belonging to groups 13–17 of the Periodic Table of the Elements, optionally $R^{11}$ and $R^{12}$, or $R^{12}$ and $R^{13}$, or $R^{13}$ and $R^{14}$ can form a ring comprising 4 to 8 atoms which can bear substitutents.

9. The metallocene compound according to claim 8, wherein $R^{14}$ is a $C_6$–$C_{20}$-aryl group and $R^{16}$ is a $C_1$–$C_{20}$-alkyl group.

10. The metallocene compound according to claim 1, wherein both Y and Z are a moiety of formula (II), A is an element of the group 16 of the Periodic Table of the Elements (new IUPAC version), B and D are carbon atoms, $R^1$ is a $C_1$–$C_{20}$-alkyl group, $R^2$ is hydrogen, $R^3$ is different from hydrogen, m is 0, n and s are 1.

11. The metallocene compound according to claim 10, wherein A is sulfur, $R^3$ is a $C_6$–$C_{20}$-aryl group or a $C_7$–$C_{20}$-alkylaryl group, the alkyl group being ortho-substituted to the aryl substituent or being a 2, 4 disubstituted phenyl group, $R^4$ is different from hydrogen, $R^5$ is hydrogen.

12. The metallocene compound according to claim 10, wherein $R^1$ is a methyl group, $R^3$ is a phenyl group, a naphthyl group, orto-methylphenyl group or 2,4-dimethylphenyl group.

13. The metallocene compound according to claim 1, wherein both Y and Z are a moiety of formula (II), L is a >C($R^{17}$)$_2$ group, $R^1$ is a hydrogen atom, $R^2$ is different from hydrogen.

14. A ligand of formula (V):

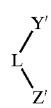

(V)

wherein Y' is a moiety of formula (VI):

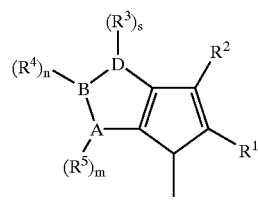

(VI)

and/or its double bond isomers;
$R^1$, $R^2$, $R^3$, $R^4$, $R^5$, A, B, D, n, m and s are as described in claim 1;
Z' is selected from a moiety of formula (VI) and from a moiety of formula (VII):

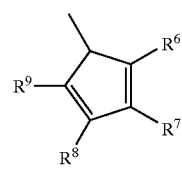

(VII)

and/or its double bond isomers;
$R^6$, $R^7$, $R^8$ and $R^9$ are as described in claim 1;
when Z' is equal to Y', A, B and D in Y' and Z' can be the same or different from each other;
L is a divalent bridge as defined in claim 1.

15. The ligand of formula (V) according to claim 14, wherein both Z' and Y' are a moiety of formula (VI), $R^1$ and $R^4$ are $C_1$–$C_{20}$-alkyl groups, $R^2$ is hydrogen, $R^3$ is a $C_6$–$C_{20}$-aryl or a $C_7$–$C_{20}$-alkylaryl group, A is selected from sulphur, selenium, tellurium and polonium, B and D are selected from the group 14 of the Periodic Table of the Elements (new IUPAC version), the divalent bridging group L is ($CH_3$)$_2$Si<, $Ph_2$Si<, >$CH_2$ or ($CH_3$)$_2$C<.

16. The ligand according to claim 14, wherein A is sulfur and B and D are carbon atoms.

17. The ligand of formula (V) according to claim 14, wherein Z' is a moiety of formula (VIII):

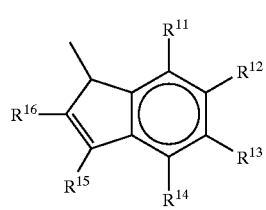

(VIII)

and/or its double bond isomers;
wherein $R^{11}$, $R^{12}$, $R^{13}$, $R^{14}$, $R^{15}$ and $R^{16}$, same or different from each other are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13–17 of the Periodic Table of the Elements, optionally $R^{11}$ and $R^{12}$, or $R^{12}$ and $R^{13}$, or $R^{13}$ and $R^{14}$ can form a ring comprising 4 to 8 atoms which can bear substitutents.

18. A process for the preparation of a ligand of formula (V) as defined in claim 14, D being a carbon atom and $R^2$ is a hydrogen, comprising the following step:
a) contacting a compound of formula (IX)

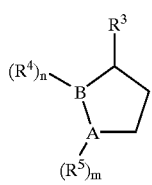

(IX)

wherein the double bonds can be in any of the allowed positions;
and wherein A, B, $R^3$, $R^4$, $R^5$, n and m are described in claim 1,
with a compound of general formula (X):

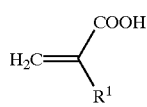

(X)

wherein $R^1$ is described in claim 1;
in the presence of a ring-closure agent, to obtain the compound of the general formula (XI):

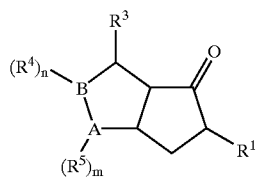

(XI)

wherein the double bonds can be in any of the allowed positions;
b) conversion into the compound of formula (XII):

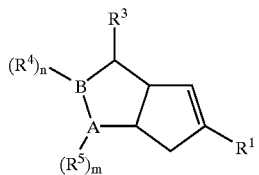

(XII)

wherein the double bonds can be in any of the allowed positions; and
when Z' is equal to Y', wherein A and B in Y' and Z' are the same or different from each other:
c1) treating the compound of formula (XII) with a base selected from hydroxides and hydrides of alkali- and earth-alkali metals, metallic sodium and potassium, and organometallic lithium salts, and subsequent contacting with a compound of formula $LQ_2$(XIII), wherein L has the same meaning as defined in claim 1, and Q is a halogen, wherein the molar ratio between the compound of formulae (XII) and (XIII) is at least 2;

or when Z' is a compound of formula (VII):
c2) treating the compound of formula (XII) with a base as defined under c1), and subsequently contacting with a compound of formula Z' LQ(XIV), wherein L has the same meaning as defined in claim 1, Z' has the same meaning as defined in claim 16 and Q is a halogen.

19. The process according to claim 18, wherein the ring-closing agent is selected from phosphorus pentoxide-methansulfonic acid (PPMA) and polyphosphoric acid (PPA); the compound of general formula (X) is methacrylic acid; the compound of general formula (IX) is 1-methyl-3-phenyl-thiophene and the reduction agent is lithium aluminum hydride (LiAlH$_4$).

20. The process according to claim 18, wherein the conversion into the compound of formula (XII) is carried out in the presence of a reduction agent and para-toulene sulfonic acid monohydrate.

21. The process according to claim 18, wherein the coupling agent used in step a) is a Ni, Pd or Pt-based coupling agent.

22. The process according to claim 18, wherein the coupling agent is bis(diphenylphosphino)propane)]dichloronickel(II) (Ni(dPPP)).

23. A process for the preparation of a metallocene compound according to claim 1, obtainable by contacting the ligand of formula (V):

(V)

wherein Y' is a moiety of formula (VI):

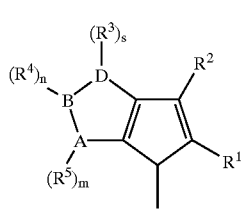

(VI)

and/or its double bond isomers;
$R^1$, $R^2$) $R^3$, $R^4$, $R^5$, A, B, D, n, m and s are as described in claim 1;
Z' is selected from a moiety of formula (VI) and from a moiety of formula (VII):

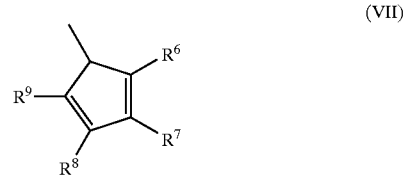

(VII)

and/or its double bond isomers,
$R^6$, $R^7$, $R^8$ and $R^9$ are as described in claim 1;
when Z' is equal to Y'', A, B and D in Y' and Z' can be the same or different from each other;
L is a divalent bridge as defined in claim 1, with a compound capable of forming a corresponding dianionic compound thereof and thereafter with a compound of formula $MX_{p+2}$, wherein M, X and p are all defined as in claim 1.

24. The process according to claim 23, wherein the compound of formula $MX_{p+2}$ is selected from titaniumtetrachloride, zirconiumtetrachloride, and hafniumtetrachloride.

25. A catalyst for the polymerization of olefins, obtainable by contacting:

A) a metallocene compound of formula (I) according to claim 1, and

B) an alumoxane and/or a compound capable of forming an alkyl metallocene cation.

26. The catalyst according to claim 25, wherein said alumoxane is obtained by contacting water with an organo-aluminum compound of formula $H_jAlR^{18}_{3-j}$ or $H_jAl_2R^{18 6-j}$, where $R^{18}$ substituents, same or different, are hydrogen atom, halogen, $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl, optionally containing silicon or germanium atoms with the proviso that at least one $R^{18}$ is different from halogen, and J ranges from 0 to 1, being also a non-integer number.

27. The catalyst according to claim 26, wherein the molar ratio between the aluminum and water is in the range of 1:1 and 100:1.

28. The catalyst according to claim 26, wherein said alumoxane is selected from the group consisting of methylalumoxane, tetra-(isobutyl)alumoxane, tetra-(2,4,4-trimethyl-pentyl)alumoxane, tetra-(2,3-dimethylbutylalumoxane, tetra-2,3,3-trimethylbutyl)alumoxane.

29. The catalyst according to claim 26, characterized in that the compound able to form a metallocene alkyl cation is a compound of formula $D^+E^-$, wherein $D^+$ is a Brønsted acid, able to give a proton and to react irreversibly with a substituent X of the metallocene of formula (I) and E is a compatible anion, which is able to stabilize the active catalytic species originating from the reaction of the two compounds, and which is sufficiently labile to be able to be removed by an olefinic monomer.

30. The catalyst according to claim 29, wherein the anion V comprises one or more boron atoms.

31. The catalyst according to claim 25 wherein said metallocene compound of formula (I) and said alumoxane and/or a compound capable of forming an alkyl metallocene cation are supported on inert supports.

32. A process for the polymerization of one or more olefins, said process comprising the polymerization reaction of one or more olefin monomers in the presence of a catalyst as claimed in claim 25.

33. The process according to claim 32, wherein the olefin monomer is propylene.

34. The process according to claim 33 wherein propylene is copolymerized with one or more alpha-olefins.

35. The process according to claim 34 wherein propylene is copolymerized with 1-butene.

36. The process according to claim 34 wherein propylene is copolymerized with ethylene.

37. The process according to claim 32 for the copolymerization of ethylene and propylene.

38. The process according to claim 32, wherein the olefin monomer is 1-butene.

* * * * *